United States Patent
Khodarev et al.

(10) Patent No.: US 9,790,504 B2
(45) Date of Patent: Oct. 17, 2017

(54) ANTI-TUMOR THERAPY

(71) Applicants: Nikolai Khodarev, Villa Park, IL (US); Ravi Sood, Seattle, WA (US); Bernard Roizman, Chicago, IL (US); Ralph R. Weichselbaum, Chicago, IL (US)

(72) Inventors: Nikolai Khodarev, Villa Park, IL (US); Ravi Sood, Seattle, WA (US); Bernard Roizman, Chicago, IL (US); Ralph R. Weichselbaum, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/893,690

(22) PCT Filed: May 21, 2014

(86) PCT No.: PCT/US2014/038885
§ 371 (c)(1),
(2) Date: Nov. 24, 2015

(87) PCT Pub. No.: WO2014/189996
PCT Pub. Date: Nov. 27, 2014

(65) Prior Publication Data
US 2016/0222387 A1 Aug. 4, 2016

Related U.S. Application Data

(60) Provisional application No. 61/827,402, filed on May 24, 2013.

(51) Int. Cl.
C12N 15/113 (2010.01)
C07H 21/02 (2006.01)
A61K 48/00 (2006.01)
A61K 31/506 (2006.01)
A61K 31/519 (2006.01)
A61K 31/713 (2006.01)
A61K 45/06 (2006.01)
C12Q 1/68 (2006.01)

(52) U.S. Cl.
CPC ........ C12N 15/1137 (2013.01); A61K 31/506 (2013.01); A61K 31/519 (2013.01); A61K 31/713 (2013.01); A61K 45/06 (2013.01); C12N 15/113 (2013.01); C12Q 1/6886 (2013.01); C12N 2310/14 (2013.01); C12N 2320/12 (2013.01); C12N 2320/30 (2013.01); C12Q 2600/136 (2013.01); C12Q 2600/158 (2013.01)

(58) Field of Classification Search
None
See application file for complete search history.

(56) References Cited

U.S. PATENT DOCUMENTS

| 2005/0255487 A1* | 11/2005 | Khvorova | A61K 31/713 435/6.11 |
| 2005/0272644 A1 | 12/2005 | Chung | |
| 2010/0040603 A1* | 2/2010 | Han | A61K 38/193 424/130.1 |
| 2010/0239656 A1 | 9/2010 | Astsaturov et al. | |
| 2013/0042333 A1 | 2/2013 | Judde et al. | |

FOREIGN PATENT DOCUMENTS

| WO | 2013/059548 A1 | 4/2013 |
| WO | 2013/072392 A1 | 5/2013 |

OTHER PUBLICATIONS

Alibadi et al (Journal of Controlled Release 172 (2013) 219-228).*
Cui et al (Hepatobiliary Pancreat. Dis. Int., 11(4): 393-400, 2012).*
Qu et al (PLoS One. 2015; 10(7): e0131285).*
Dermer (Biotechnology 12: 320, 1994).*
Mehta et al (Anticancer Research 27: 1295-1300 (2007)).*
Gillet (Proc. Nat. Acad. Sci. USA 108(46):18708-18713, 2011).*
Gillet et al (J. Nat. Cancer Inst. doi: 10.1093/jnci/djt007 7 pages, Feb. 21, 2013).*
Horvath (Nature Reviews Drug Discovery 15:751-769, Nov. 2016).*
Widau et al (Proc Natl Acad Sci U S A. Jan. 28, 2014;111(4):E484-91).*
International Search Report and Written Opinion issued in PCT application No. PCT/US14/388885, mailed Oct. 8, 2014; 9 pages.

* cited by examiner

Primary Examiner — Richard Schnizer
(74) Attorney, Agent, or Firm — Quarles & Brady LLP

(57) ABSTRACT

Panels, compositions, and methods for treating cancer in a subject in need thereof are disclosed involving one or more genes the suppression of which renders the cancer chemosensitive and/or radiosensitive.

5 Claims, 18 Drawing Sheets

Flow cytometry validation of candidate target genes identified in siRNA screen. Double-positive cells, presented in the upper right quadrant of the each panel were quantified as the measure of cell death induced by siRNA suppression of the given gene without (e) or with (f) irradiation. Gene used in these experiments is DHx58 (LGP2)

Individual siRNA against PSMB9 and PSMB10 inhibit expression of corresponding proteins in breast cancer tumor cell line MDA-MB-231 and glioblastoma cell line D54

Inhibition of PSMB9 suppresses cell growth of breast cancer cell line MDA-MB-231 and glioblastoma cell line D54

Inhibition of PSMB9 and PSMB10 leads to the increased radiation killing of breast cancer cell line MDA-MB-231.

Inhibition of PSMB9 and PSMB10 leads to the increased radiation killing of glioblastoma cell line D54.

Overexpression of USP18 increases radioresistance of glioblastoma cell lines U87 and D54 and head&neck cancer cell line SCC61.

Overexpression of USP18 increases radioresistance of xenografted D54 tumors in nude mice.

ANTI-TUMOR THERAPY

CROSS-REFERENCE TO RELATED APPLICATIONS

This application represents the U.S. National Stage of International Application No. PCT/US2014/038885, filed May 21, 2014 which is based on, claims priority to, and incorporates herein by reference in its entirety, U.S. Provisional Patent Application Ser. No. 61/827,402, filed May 24, 2013, and entitled, "Anti-Tumor Therapy."

STATEMENT CONCERNING GOVERNMENT INTEREST

Not applicable

SEQUENCE LISTING

Not applicable

BACKGROUND OF THE INVENTION

1. Field of the Invention

The present invention relates to the identification and control of gene targets for treatment of cancers, including chemoresistant and/or radioresistant cancers.

2. Description of the Background of the Invention

Cancer is not fully understood on a molecular level and remains a leading cause of death worldwide. One of the deadliest forms of cancer is solid tumors. One such solid tumor is lung cancer, the most common cancer worldwide and the leading cause of cancer-related death in the United States. Approximately 219,000 new diagnoses and over 159,000 deaths from lung cancer occur annually in the United States. Approximately 85% of lung cancers are non-small cell histology (NSCLC), including lung adenocarcinomas, which are the most common lung cancer type in the U.S. Treatment of early and intermediate stage NSCLC usually involves surgery, stereotactic radiotherapy, or conventional radiotherapy with or without adjuvant chemotherapy. Chemotherapy regimens for lung cancer, either concurrent with radiotherapy (RT) or adjuvant to surgery, usually incorporate platinum-based drugs such as cisplatin or carboplatin, as this has been shown to confer a survival advantage when either combined with radiotherapy or in the adjuvant setting.

Standard fractionated radiotherapy as the primary treatment for NSCLC is reserved for patients with tumors too advanced to resect, who are medically unstable, whose disease has spread beyond the chest, or in the case of small or metastatic tumor hypofractionated stereotacktic body radiotherapy. The utility of postoperative radiotherapy is controversial and subsets of patients who are likely to benefit have been proposed. These include patients with advanced lymph node metastases (N2-N3 or extra-capsular extension) and close or positive surgical margins. However, clear clinical and/or molecular selection criteria for patients who may benefit from postoperative radiotherapy remains elusive. No prognostic or predictive signature to select patients with NSCLC who may benefit from radiotherapy or chemotherapy is consistently used in clinical practice at this time.

The activity of Jak/Stat dependent genes has been shown to predict the outcome of patients with lung cancer and their response to the adjuvant radiotherapy or chemotherapy. Stat1 (Signal Transducer and Activator of Transcription 1) is a member of the Stat family of proteins, which are mediators of Jak signaling. Stat1 is phosphorylated at the tyrosine 701 position by Jak kinases and translocates to the nucleus to activate the transcription of hundreds of Interferon-Stimulated Genes (ISGs).

Further, clinical trials of Jak/Stat pathway inhibitors in hematological malignancies are ongoing for the pharmacological suppression of the Stat-related pathways. Jak inhibitors currently available include either specific inhibitors of Jak2 or combined inhibitors of Jak1 and Jak2. The radiosensitizing effects of the Jak2 inhibitor TG101209 (TargeGen Inc., CAS 936091-14-4) were recently described in two lung cancer cell lines and were associated with suppression of the Stat3 pathway. TG101209 was developed to potentially inhibit myeloproliferative disorder-associated JAK2V617F and MPLW515L/K mutations. Activation of Jak2/Stat3 signaling was demonstrated in several other lung cancer cell lines and was associated with increased oncogenic potential, tumor angiogenesis, and EGFR signaling associated with progression of lung adenocarcinomas. Further, next-generation sequencing recently revealed constitutively active Jak2 mutation (V617F) in some lung cancer patients.

To date, few publications describe the application of these drugs in lung cancer models, and mechanisms of their action in lung cancer are still poorly understood. The majority of publications regarding the application of Jak inhibitors in solid tumors, including lung cancer, explain their action based on pathways activated by Stat3, Stat5 or not directly related to Stat signaling. Jak/Stat1 pathways in solid tumors are not described in the context of therapeutic effects of Jak inhibitors, though they are already described in some myelodysplastic diseases. It is believed that Jak1 kinase is activated by Jak2 kinase and both are necessary for activation of Stat1 and Stat3. It is also believed that Stat1 and Stat3 can form heterodimers with transcriptional activity. Additionally, genes induced by Jak2/Stat3 activation overlap with IFN/Stat1-dependent genes. Finally, constitutively active oncogenic Jak2 (Jak2V617F) induces genes overlapping with the Stat1-dependent genes.

While the importance of Jak/Stat signaling, in general, for cancers continues to be investigated, the role that downstream effector genes may play in tumors remains undefined. Consequently, there is an urgent and definite need to identify the downstream effector genes that may potentially have a role in tumor development associated with activation of the Jak/Stat pathway. Such genes may provide new targets for Jak-related therapy of cancers, including, for example, lung cancer, or for sensitization of cancers for chemotherapies and/or radiotherapies. Therefore, there is a need to determine the identities of downstream effector genes in the Jak/Stat pathway of cancer, including solid tumors, that may play a role in treating cancers, and to develop effective cancer therapies around these downstream effector genes. More effective and targeted cancer therapies with potentially fewer side effects are also needed.

SUMMARY OF THE INVENTION

According to a first aspect, a panel for treating a cancer in a subject in need thereof includes one or more genes contributing to tumor development or chemoresistance and/or radioresistance of a cancer cell. Suppression of the one or more genes results in at least one of suppression of growth or proliferation of the cancer cell, cell death of the cancer cell, or sensitization of the cancer cell to chemotherapy and/or radiotherapy.

In one embodiment, the cancer is Jak/Stat dependent.

In another embodiment, the cancer is associated with activation of a Jak/Stat-related pathway.

Illustratively, Jak includes a Jak-1, a Jak-2, a Jak-3 or a Tyk2 kinase, and the Stat includes a Stat1, a Stat2, a Stat 3, a Stat4, a Stat5, or a Stat6 transcriptional factor In another embodiment, the one or more genes of the panel is an interferon stimulated gene.

In a further embodiment, the one or more genes of the panel includes, for example, DHX58 (LGP2), PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14.

According to a second aspect, a panel for treating a cancer in a subject in need thereof includes one or more inhibitors of expression specific for one or more genes including, for example, DHX58, PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, or TRIM14. Administration of the one or more inhibitors of expression to a cancer cell results in, for example, at least one of: suppression of growth or proliferation of the cancer cell, cell death of the cancer cell, or sensitization of the cancer cell to chemotherapy and/or radiotherapy.

In one embodiment, the one or more inhibitors of expression and/or functional activity comprises an siRNA molecule, an shRNA molecule, a micro-RNA molecule, a small molecule, a peptide inhibitor, or a combination or a pharmaceutically acceptable salt or prodrug thereof. The one or more inhibitors of expression and/or functional activity is in a therapeutically effective amount and formulated for administration to the subject.

In another embodiment, the panel comprises inhibitors of expression and/or functional activity specific for at least two genes including, for example, DHX58, PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14.

In one embodiment, administration to the subject of one or more antineoplastic agents and radio therapy results in at least one of suppression of growth or proliferation of the cancer cell, or cell death of the cancer cell.

In a further embodiment, administration of the one or more antineoplastic agents or radio therapy is subsequent to the administration of the inhibitor of expression and/or functional activity.

According to a third aspect, a kit for treating cancer in a subject in need thereof includes a panel comprising one or more inhibitors of expression and/or functional activity specific for one or more genes including, for example, DHX58, PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14. The kit further includes an antineoplastic agent, which may be optional in some embodiments.

In one embodiment, the kit further includes at least one of a Jak2 or a Jak1/Jak2 inhibitor in a therapeutically effective amount.

In another embodiment, the Jak 2 inhibitor is SAR302503.

In a further embodiment, the Jak1/Jak2 inhibitor is Ruxolitinib.

In a fourth aspect, a method of treating a cancer in a subject in need thereof includes: a) suppression of at least one gene in the subject in a therapeutically effective amount, the gene includes, for example, DHX58, PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14; and b) administration to the subject a therapeutically effective amount of at least one of an antineoplastic agent or radio therapy.

In one embodiment, the method further includes administration to the subject a therapeutically effective amount of at least one of a Jak2 or a Jak1/Jak2 inhibitor.

In a further embodiment, the therapeutically effective amount of gene suppression is sufficient to render the cancer chemosensitive or radiosensitive.

In another embodiment, the therapeutically effective amount of gene suppression is less than or equal to about 75% of normal gene activity.

In a fifth aspect, a pharmaceutical composition includes a therapeutically effective amount of an agent that suppresses at least one gene in a subject, the gene includes, for example, DHX58, PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14. The pharmaceutical composition includes one or more pharmaceutically acceptable carriers, diluents and excipients.

In one embodiment, the composition further includes a therapeutically effective amount of at least one of an antineoplastic agent or a radiotherapy agent.

In another embodiment, the pharmaceutical composition is formulated to be administered to the subject in at least one of an oral, inhalation, parental injection, topical, or suppository dosage form.

DESCRIPTION

Figure 1:
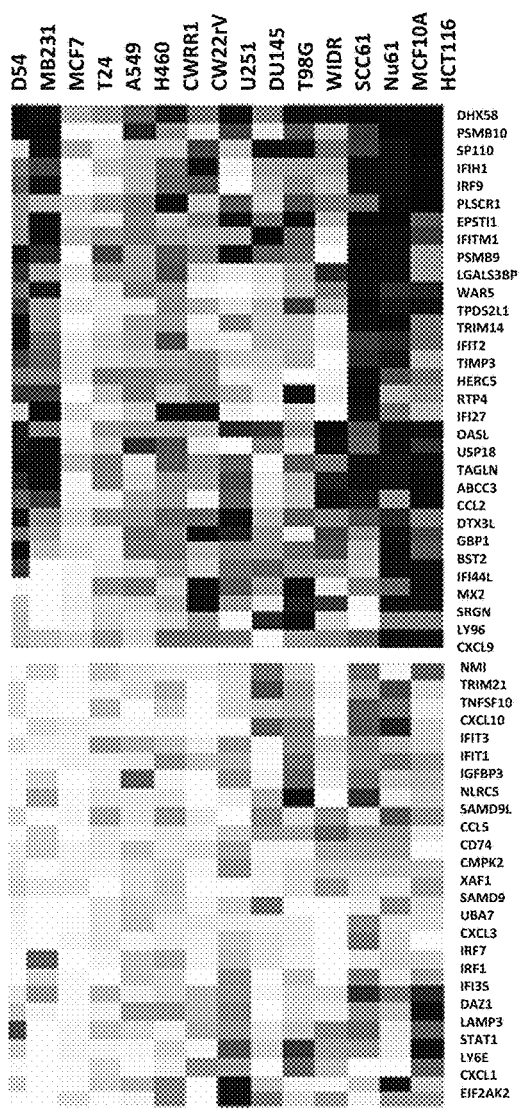
FIG. 1 shows a heat map of a phenotypic screen for selected genes using a panel of siRNAs in 16 cell lines representing 7 types of cancer (lung, breast, prostate, colon, bladder, head and neck and glioblastoma multiforme (GBM)). Blue represents suppression of cell viability in the result of suppression of the given gene and yellow-increase of viability. Genes for which suppression leads to lost viability potentially confer growth/survival of tumor cells. Eight genes were selected based on their ability to suppress survival in the majority of cell lines tested independently of cancer type. One gene (MCL1) was selected as an example of cancer-type specific gene (knock-down of MCL1 led to the maximal suppression of survival in 2 cell lines representing hormone-independent prostate cancer). Data indicate that suppression of one or more of these genes alone or in combination with ionizing radiation (IR) (and/or chemotherapy) may increase killing of tumor cells as compared with ionizing radiation (or chemotherapy)

Treatment of a cancer in a subject in need thereof is provided herein, as are compositions, kits, and methods for treating cancer, and methods for identifying effector genes in the Jak/Stat pathway having a role in the treatment of cancer and therapies to treat cancer based on these effector genes. A Jak/Stat dependent cancer may include any solid tumor, including lung, prostate, head and neck, breast and colorectal cancer, melanomas and gliomas, and the like. While the present disclosure may be embodied in different forms, several specific embodiments are discussed herein with the understanding that the present disclosure is to be considered only an exemplification and is not intended to limit the invention to the illustrated embodiments.

While not wishing to be bound by theory, it is believed that downstream effector genes in the Jak/Stat pathway have a causal role in treatment-resistant cancers, including solid tumors, such as lung cancer. Therefore, if downstream effector genes could be identified to have a direct relationship to treatment resistance, new therapies could be developed for treatment resistant cancers. One approach for determining downstream effector genes that have a direct role in treatment resistance is to suppress the gene and determine whether a treatment resistant cancer cell with the suppressed gene becomes treatment sensitive. In experimental models using knock-downs of Stat1, suppression of Stat1 and subsequent suppression of down-stream genes activated by Stat1 lead to radiosensitization, chemosensitization to doxorubicin, and/or growth suppression of cancer. These genes in the Stat1 pathway may provide targets for personalized therapy of cancer, including lung cancer. Further, implementing siRNA screening technologies, several Stat1-dependent genes were detected as candidates for conferring tumor resistance to genotoxic stress and protection from apoptosis.

Another potential step in this process is to identify gene candidates. One approach is to use available microarray and proteomics data to identify potential candidates. Criteria for selection may include control by the Jak/Stat pathway, association with oncogenesis and/or radio/chemoresistance, and/or dysregulation in cancerous (or precancerous) tissues. Additional criteria may also be chosen and combined for selection.

Another potential step is to suppress expression or otherwise inhibit the gene or resultant protein of the candidate gene. One method to achieve expression inhibition is siRNA. Other methodologies known in the art may be used, such as, for example, small hairpin RNA (shRNA), micro-RNAs, small molecules, peptide inhibitors, combinations thereof, and the like.

A further step can include administering an antineoplastic agent (e.g., chemotherapy) and/or radiotherapy to a treatment resistant cancer cell in which the candidate downstream effector gene is suppressed. A loss of viability of the treatment resistant cancer cell reveals that that candidate downstream effector gene may be an effective target for therapy.

An illustrative antineoplastic agent or chemotherapeutic agent includes, for example, a standard taxane. Taxanes are produced by the plants of the genus *Taxus* and are classified as diterpenes and widely uses as chemotherapy agents including, for example, paclitaxel, (Taxol®, Bristol-Meyers Squibb, CAS 33069-62-4) and docetaxel (Taxotere®, Sanofi-Aventis, CAS 114977-28-5). Other chemotherapeutic agents include semi-synthetic derivatives of a natural taxoid such as cabazitaxel (Jevtana®, Sanofi-Aventis, CAS 183133-96-2). Other chemotherapeutic agents also include an androgen receptor inhibitor or mediator. Illustrative androgen receptor inhibitors include, a steroidal antiandrogen (for example, cyperterone, CAS 2098-66-0); a non-steroidal antiandrogen (for example, flutamide, Eulexin®, Schering-Plough, CAS 13311-84-7); nilutamide (Nilandron, CAS 63612-50-0); enzalutamide (Xtandi®, Medivation®, CAS 915087-33-1); bicalutamide (Casodex, AstraZeneca, CAS 90357-06-5); a peptide antiandrogen; a small molecule antiandrogen (for example, RU58642 (Roussel-Uclaf SA, CAS 143782-63-2); LG120907 and LG105 (Ligand Pharmaceuticals); RD162 (Medivation, CAS 915087-27-3); BMS-641988 (Bristol-Meyers Squibb, CAS 573738-99-5); and CH5137291 (Chugai Pharmaceutical Co. Ltd., CAS 104344603904)); a natural antiandrogen (for example, ataric acid (CAS 4707-47-5) and N-butylbensensulfonamide (CAS 3622-84-2); a selective androgen receptor modulator (for example, enobosarm (Ostarine®, Merck & Company, CAS 841205-47-8); BMS-564,929 (Bristol-Meyer Squibb, CAS 627530-84-1); LGD-4033 (CAS 115910-22-4); AC-262,356 (Acadia Pharmaceuticals); LGD-3303 (Ganolix Lifescience Co., Ltd., 9-chloro-2-ethyl-1-methyl-3-(2,2,2-trifluoro-ethyl)-3H-pyrrolo [3,2-f]quinolin-7(6H)-one; S-40503, Kaken Pharmaceuticals, 2-[4-(dimethylamino)-6-nitro-1,2,3,4-tetrahydroquinolin-2-yl]-2-methylpropan-1-ol); andarine (GTx-007, S-4, GTX, Inc., CAS 401900-40-1); and S-23 (GTX, Inc., (2S)—N-(4-cyano-3-trifluoromethylphenyl)-3-(3-fluoro-4-chlorophenoxy)-2-hydroxy-2-methyl-propanamide)); or those described in U.S. Patent Appln. No. 2009/0304663. Other neoplastic agents or chemotherapeutic agents that may be used include, for example: alkylating agents such as nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; biological response modifiers such as interferon alphenomes; other agents such as platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MTH); adrenocortical suppressant such as mitotane (o,p'-DDD) and aminoglutethimide; taxol analogues/derivatives; hormone agonists/antagonists such as flutamide and tamoxifen; and GnRH and analogues thereof. Examples of other chemotherapeutic can be found in Cancer Principles and Practice of Oncology by V. T. Devita and S. Hellman (editors), 6.sup.th edition (Feb. 15, 2001), Lippincott Williams & Wilkins Publishers.

Radiotherapy is based on ionizing radiation delivered to a target area that results in death of reproductive tumor cells. Some examples of radiotherapy include the radiation of cesium, palladium, iridium, iodine, or cobalt and is usually delivered as ionizing radiation delivered from a linear accelerator or an isotopic source such as a cobalt source. Also variations on linear accelerators are Cyberkine and Tomotherapy. Particle radiotherapy from cyclotrons such as Protons or Carbon nuclei may be employed. Also radioisotopes delivered systemically such as p32 or radium 223 may be used. The external radiotherapy may be systemic radiation in the form of sterotacktic radiotherapy total nodal radiotherapy or whole body radiotherapy but is more likely focused to a particular site, such as the location of the tumor or the solid cancer tissues (for example, abdomen, lung, liver, lymph nodes, head, etc.). The radiation dosage regimen is generally defined in terms of Gray or Sieverts time and fractionation, and must be carefully defined by the radiation oncologist. The amount of radiation a subject receives will depend on various consideration but the two important considerations are the location of the tumor in relation to other critical structures or organs of the body, and the extent to which the tumor has spread. One illustrative course of treatment for a subject undergoing radiation therapy is a treatment schedule over a 5 to 8 week period, with a total dose of 50 to 80 Gray (Gy) administered to the subject in a single daily fraction of 1.8 to 2.0 Gy, 5 days a week. A Gy is an abbreviation for Gray and refers to 100 rad of dose.

Radiotherapy can also include implanting radioactive seeds inside or next to an site designated for radiotherapy and is termed brachytherapy (or internal radiotherapy, endocurietherapy or sealed source therapy). For prostate cancer, there are currently two types of brachytherapy: permanent and temporary. In permanent brachytherapy, radioactive (iodine-125 or palladium-103) seeds are implanted into the prostate gland using an ultrasound for guidance. Illustratively, about 40 to 100 seeds are implanted and the number and placement are generally determined by a computer-generated treatment plan known in the art specific for each subject. Temporary brachytherapy uses a hollow source placed into the prostate gland that is filled with radioactive material (iridium-192) for about 5 to about 15 minutes, for example. Following treatment, the needle and radioactive material are removed. This procedure is repeated two to three times over a course of several days.

Radiotherapy can also include radiation delivered by external beam radiation therapy (EBRT), including, for example, a linear accelerator (a type of high-powered X-ray machine that produces very powerful photons that penetrate deep into the body); proton beam therapy where photons are derived from a radioactive source such as iridium-192, caesium-137, radium-226 (no longer used clinically), or colbalt-60; Hadron therapy; multi-leaf collimator (MLC); and intensity modulated radiation therapy (IMRT). During this type of therapy, a brief exposure to the radiation is given for a duration of several minutes, and treatment is typically given once per day, 5 days per week, for about 5 to 8 weeks. No radiation remains in the subject after treatment. There are several ways to deliver EBRT, including, for example, three-dimensional conformal radiation therapy where the beam intensity of each beam is determined by the shape of the tumor. Illustrative dosages used for photon based radiation is measured in Gy, and in an otherwise healthy subject (that is, little or no other disease states present such as high blood pressure, infection, diabetes, etc.) for a solid epithelial tumor ranges from about 60 to about 80 Gy, and for a lymphoma ranges from about 20 to about 40 Gy. Illustrative preventative (adjuvant) doses are typically given at about 45 to about 60 Gy in about 1.8 to about 2 Gy fractions for breast, head, and neck cancers.

When radiation therapy is a local modality, radiation therapy as a single line of therapy is unlikely to provide a cure for those tumors that have metastasized distantly outside the zone of treatment. Thus, the use of radiation therapy with other modality regimens, including chemotherapy, have important beneficial effects for the treatment of metastasized cancers.

Radiation therapy has also been combined temporally with chemotherapy to improve the outcome of treatment. There are various terms to describe the temporal relationship of administering radiation therapy and chemotherapy, and the following examples are illustrative treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it were given alone.

It should be noted that other therapeutically effective doses of radiotherapy can be determined by a radiation oncologist skilled in the art and can be based on, for example, whether the subject is receiving chemotherapy, if the radiation is given before or after surgery, the type and/or stage of cancer, the location of the tumor, and the age, weight and general health of the subject.

It is further contemplated that subsets of gene targets, including those identified or described herein, could be used as a therapeutic tool for diagnosing and/or treating a tumor or cancer. For example, siRNA pools (or other sets of molecules individually specific for one or more predetermined targets including, for example, shRNA pools, small molecules, and/or peptide inhibitors, collectively "expression inhibitors" or "active ingredients" or "active pharmaceutical ingredients") may be generated based on one or more (e.g., 2 or 4 or 8 or 12, or any number) targets and used to treat a subject in need thereof (e.g., a mammal having a chemoresistant or radioresistant cancer). Upon rendering of the subject's cancer chemosensitive and/or radiosensitive, therapeutic intervention in the form of antineoplastic agents and/or ionizing radiation as known in the art (see for example, U.S. Pat. No. 6,689,787, incorporated by reference) may be administered to reduce and/or eliminate the cancer. It is contemplated that therapeutic intervention may occur before, concurrent, and/or subsequent to the treatment to render the subject chemosensitive or radiosensitive. It is further envisioned that particular subsets of targets may be advantageous over others based on the particular type of cancer and/or tissue of origin for providing a therapeutic effect. Administration of such therapies may be accomplished by any means known in the art.

In one embodiment, a kit may include a panel of siRNA pools directed at one or more targets as identified by or in the present disclosure, including those targets identified in Table Nos. 4a and 4b, below. It is envisioned that a particular kit may be designed for a particular type of cancer and/or a specific tissue. The kit may further include means for administering the panel to a subject in need thereof. In addition, the kit may also include one or more antineoplastic agents directed at the specific type of cancer against which the kit is directed and one or more compounds that inhibit that Jak/Stat pathway.

Kits may further be a packaged collection of related materials, including, for example, a single and/or a plurality of dosage forms each approximating an therapeutically effective amount of an active ingredient, such as, for example, an expression inhibitor and/or a pharmaceutical compound as described herein that slows, stops, or reverses the growth or proliferation of a tumor or cancer or kills tumor or cancer cells, and/or an additional drug. The included dosage forms may be taken at one time, or at a prescribed interval. Contemplated kits may include any combination of dosage forms.

In another embodiment, a method of treating a subject in need thereof includes administering to the subject one or more molecules that target one or more genes of Table Nos. 4a and 4b, such as siRNA and/or shRNA pools. The method may further include, for example, treatment of the subject with one or more antineoplastic agents, ionizing radiation, and/or one or more compounds that inhibit that Jak/Stat pathway.

Suppression of a gene refers to the absence of expression of a gene or a decrease in expression of a gene as compared to the activity of an untreated gene. Suppression of a gene may be determined by detecting the presence or absence of expression of a gene or by measuring a decrease of expression of a gene by any means known in the art including, for example, detecting a decrease in the level of the final gene product, such as a protein, or detecting a decreased level of a precursor, such as mRNA, from which gene expression levels may be inferred when compared to normal gene activity, such as a negative (untreated) control. Any molecular biological assay to detect mRNA or an immunoassay to detect a protein known in the art can be used. A molecular biological assay includes, for example, polymerase chain reaction (PCR), Northern blot, Dot blot, or an analysis method with microarray or macroarray. An immunological assay includes, for example, ELISA (enzyme-linked immunosorbent assay) with a microtiter plate, radioimmunoassay (RIA), a fluorescence antibody technique, Western blotting, or an immune structure dyeing method. Suppression of a gene may also be inferred biologically in vivo, in situ, and/or in vitro, by the suppression of growth or proliferation of a tumor or cancer cell, cell death of a tumor or cancer cell, and/or the sensitization of a tumor or cancer cell to chemotherapy and/or radiotherapy. Illustratively, a therapeutically effective amount of gene suppression in a subject results in the suppression of growth or proliferation of a tumor or cancer cell, cell death of the tumor or cancer cell, and/or the sensitization of the tumor or cancer cell to chemotherapy and/or radiotherapy. As each subject is different and each cancer is different, the amount of gene suppression to achieve a therapeutically effective amount of gene suppression may be determined by a trained professional skilled in the area on a case-by-case basis. Illustratively, a therapeutically effective amount of gene suppression may include, for example, less than or equal to about 95% of normal gene activity, or less than or equal to about 90% of normal gene activity, or less than or equal to about 85% of normal gene activity, or less than or equal to about 80% of normal gene activity, or less than or equal to about 75% of normal gene activity, or less than or equal to about 65% of normal gene activity, or less than or equal to about 50% of normal gene activity, or less than or equal to about 35% of normal gene activity, or less than or equal to about 25% of normal gene activity, or less than or equal to about 15% of normal gene activity, or less than or equal to about 10% of normal gene activity, or less than or equal to about 7.5% of normal gene activity, or less than or equal to about 5% of normal gene activity, or less than or equal to about 2.5% of normal gene activity, or less than or equal to about 1% of normal gene activity, or less than or equal to about 0% of normal gene activity.

Suppression of identified genes individually or in combination combined with ionizing radiation and/or any chemotherapeutic agents may improve the outcome of patients treated with the ionizing radiation or any chemotherapy agent or any treatment designed to improve outcome of the cancer patients (like Jak1/Jak2 inhibitors) if such treatment is combined with the suppression of any of these genes or their combination.

Based on the functional groups, we also contemplate that suppression of the chemokine signaling, or suppression of negative regulators of interferon response, or suppression of protein degradation or mitochondria-related anti-apoptotic molecules or anti-viral proteins or extracellular matrix proteins (ECM) alone or in combination with ionizing radiation or any chemotherapy drug or any treatment designed to improve outcome of the cancer patients will improve cancer treatment. This is based on the functional associations between detected targets. DHX58 (also known as LGP2) is known as an apical suppressor of RNA dependent activation of the Type I interferons alpha and beta. IFITM1 and OASL are known anti-viral proteins. USP18 and HERC5 are enzymes involved in protein ISGylation/de-ISGylation, known to protect proteins from ubiquitin-dependent degradation in proteosome complex, while PSMB9 and PSMB10 are proteasome subunits. EPSTL1, LGALS3P and TAGLN are involved in the structure and functional regulation of ECM. CXCL9 and CCL2 are chemokines with multiple functions including growth-promoting functions for tumor cells.

Jak (Janus kinase) refers to a family of intracellular, nonreceptor tyrosine kinases and includes four family members, Janus 1(Jak-1), Janus 2 (Jak-2), Janus 3 (Jak-3), and Tyrosine kinase 2 (Tyk2).

Stat (Signal Transducer and Activator of Transcription) plays a role in regulating cell growth, survival and differentiation and the family includes Stat1, Stat2, Stat3, Stat4, Stat5 (Stat5a and Stat5b), and Stat6.

The term "subject" refers to any organism classified as a mammal, including mice, rats, guinea pigs, rabbits, dogs, cats, cows, horses, monkeys, and humans.

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

As used herein, the phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this invention.

As used herein, the term "chemoresistant" refers to a tumor or cancer cell that shows little or no significant detectable therapeutic response to an agent used in chemotherapy.

As used herein, the term "radioresistant" refers to a tumor or cancer cell that shows little or no significant detectable therapeutic response to an agent used in radiotherapy such as ionizing radiation.

As used herein, the term "chemosensitive" refers to a tumor or cancer cell that shows a detectable therapeutic response to an agent used in chemotherapy.

As used herein, the term "radiosensitive" refers to a tumor or cancer cell that shows a detectable therapeutic response to an agent used in radiotherapy.

As used herein, the phrases "chemotherapeutic agent," "cytotoxic agent," "anticancer agent," "antineoplastic agent" and "antitumor agent" are used interchangeably and refer to an agent that has the effect of inhibiting the growth or proliferation, or inducing the killing, of a tumor or cancer cell. The chemotherapeutic agent may inhibit or reverse the development or progression of a tumor or cancer, such as for example, a solid tumor.

As used herein, the term "chemotherapy" refers to administration of at least one chemotherapeutic agent to a subject having a tumor or cancer.

As used herein, the term "radiotherapy" refers to administration of at least one "radiotherapeutic agent" to a subject having a tumor or cancer and refers to any manner of treatment of a tumor or cancer with a radiotherapeutic agent. A radiotherapeutic agent includes, for example, ionizing radiation including, for example, external beam radiotherapy, stereotatic radiotherapy, virtual simulation, 3-dimensional conformal radiotherapy, intensity-modulated radiotherapy, ionizing particle therapy and radioisotope therapy.

Compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Eston, Pa.; 18.sup.th edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benezenesulfonic, salicyclic sulfanilic, aspartic, glutamic, edetic, stearic, palmitic, oleic, lauric, pantothenic, tannic, ascorbic, and valeric acids.

Various pharmaceutically acceptable salts include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc. A solvate may be a pharmaceutically suitable (i.e., pharmaceutically acceptable) solvate, whereby solvation is an interaction of a solute with a solvent that leads to stabilization of the solute species in a solution, and whereby the solvated state is an ion in a solution complexed by solvent molecules. Solvates and hydrates may also be referred to as "analogues."

A prodrug may be a compound that is pharmacologically inert but is converted by enzyme or chemical action to an active form of the drug (i.e., an active pharmaceutical ingredient) at or near the predetermined target site. In other words, prodrugs are inactive compounds or partially active compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug (e.g., active ingredient) with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction. A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein.

Dosage form compositions containing the active ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)

(7). Alcohol is a good example of an ingredient that may be considered either active or inactive depending on the product formulation.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

A transdermal dosage form may include, but is not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosage regimen to be employed may vary widely and may necessarily deviate from the dosage regimens set forth herein.

Contemplated dosage forms may include an amount of one or more expression inhibitors (or inhibitors of expression) ranging from about 1 to about 1200 mg, or about 5 to about 100 mg, or about 25 to about 800 mg, or about 100 to about 500 mg, or 0.1 to 50 milligrams (±10%), or 10 to 100 milligrams (±10%), or 5 to 500 milligrams (±10%), or 0.1 to 200 milligrams (±10%), or 1 to 100 milligrams (±10%), or 5 to 50 milligrams (±10%), or 30 milligrams (±10%), or 20 milligrams (±10%), or 10 milligrams (±10%), or 5 milligrams (±10%), per dosage form, such as, for example, a tablet, a pill, a bolus, and the like.

In another embodiment, a dosage form may be administered to a subject in need thereof once per day, or twice per day, or once every 6 hours, or once every 4 hours, or once every 2 hours, or hourly, or twice an hour, or twice a day, or twice a week, or monthly.

The phrase "therapeutically effective" is intended to qualify the amount that will achieve the goal of improvement in disease severity and/or the frequency of incidence over non-treatment, while limiting, reducing, or avoiding adverse side effects typically associated with disease therapies. A "therapeutic effect" relieves to some extent one or more of the symptoms of a cancer disease or disorder. In reference to the treatment of a cancer, a therapeutic effect refers to one or more of the following: 1) reduction in the number of cancer cells by, for example, killing the cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anti-cancer agents. "Therapeutic effective amount" is intended to qualify the amount required to achieve a therapeutic effect.

A therapeutically effective amount of an expression inhibitor (or inhibitors of expression) may be any amount that begins to improve cancer treatment in a subject. In one embodiment, an effective amount of an expression inhibitor used in the therapeutic regime described herein may be, for example, about 1 mg, or about 5 mg, or about 10 mg, or about 25 mg, or about 50 mg, or about 100 mg, or about 200 mg, or about 400 mg, or about 500 mg, or about 600 mg, or about 1000 mg, or about 1200 mg, or about 1400 mg, or from about 10 to about 60 mg, or about 50 mg to about 200 mg, or about 150 mg to about 600 mg per day. Further, another effective amount of an expression inhibitor used herein may be that which results in a detectable blood level of above about 1 ng/dL, 5, ng/dL, 10 ng/dL, 20 ng/dL, 35 ng/dL, or about 70 ng/dL, or about 140 ng/dL, or about 280 ng/dL, or about 350 ng/dL, or lower or higher.

The term "pharmaceutically acceptable" is used herein to mean that the modified noun is appropriate for use in a pharmaceutical product. Pharmaceutically acceptable cations include metallic ions and organic ions. Other metallic ions include, but are not limited to appropriate alkali metal salts, alkaline earth metal salts and other physiological acceptable metal ions. Exemplary ions include aluminium, calcium, lithium, magnesium, potassium, sodium and zinc in their usual valences. Organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

It is further contemplated that one active ingredient may be in an extended release form, while an optional second, third, or fourth other active ingredient, for example, may or may not be, so the recipient experiences, for example, a spike in the second, third, or fourth active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Solutions or suspensions may be applied topically and/or directly to the nasal cavity, respiratory tract, eye, or ear by conventional means, for example with a dropper, pipette or spray.

Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form.

The present disclosure is further illustrated by the following examples, which should not be construed as limiting in any way. The contents of all cited references throughout this application are hereby expressly incorporated by reference. The practice of the present invention will employ, unless otherwise indicated, conventional techniques of pharmacology and pharmaceutics, which are within the skill of the art.

EXAMPLES

Materials and Methods

Cell Lines

Cell lines were from the American Type Culture Collection (Rockville, Md.), except for CW22Rv1 and CWRR1, which were kindly provided by Dr. Donald VanderGriend, the University of Chicago.

Western Blotting and Flow Cytometry

Total cellular protein was extracted in radioimmunoprecipitation assay buffer with protease inhibitors added (1×PBS, 1% NP40, 0.5% sodium deoxycholate, 0.1% SDS, 1 mmol/L $Na_3VO_4$, 2 μg/mL aprotinin, 1 mmol/L phenylmethylsulfonyl fluoride). All samples were normalized by protein concentration using Bradford reagent and standard solution of bovine serum albumin (1 mg/mL). Concentration of all samples was adjusted to 1 mg/mL and equal amount of protein was loaded in each well. For total proteins, 10 μg of protein was loaded per well. Proteins were separated on 7.5%-12% SDS-PAGE (depending on molecular mass of protein) and transferred to polyvinylidene difluoride membranes (PVDF). Total proteins were detected using the rabbit or goat primary Abs. For loading control, the antibodies for actin (I-19) and glyceraldehyde-3-phosphate dehydrogenase (GAPDH; FL-335) were used. All antibodies were purchased from Santa Cruz Biotechnology. Images were quantified with ImageJ software by integration pixel values across the area of specific bands.

Real-Time PCR Analysis cDNA was synthesized as described previously (see, Khodarev N N, Yu J, Nodzenski E, et al. Method of RNA purification from endothelial cells for DNA array experiments. Biotechniques 2002; 32: 316-20). For the internal control, GAPDH was used. PCR was done for 40 cycles at 95° C. for 15 s and 60° C. for 1 min after initial incubations at 50° C. for 2 min and 95° C. for 10 min using SYBR Green PCR reagent in ABI 7700 System (Applied Biosystems). ΔCt values were calculated according to the manufacturer's instructions. Fold induction/suppression relative to GAPDH was calculated as $2^{-\Delta Ct}$. Fold induction of gene $X_{si}$ in gene-specific siRNA transfected cell line relative to gene $X_{nt}$ in the same cell line transfected by non-targeting siRNA was calculated as $2^{-(\Delta\Delta Ct X)}$, where ΔCt values of all control replicates were averaged. Number of replicates per each group varied from three to six in different experiments.

Example 1. Identification of Downstream Effector Genes of the Jak/Stat Pathway To identify downstream effector genes in the Jak/Stat pathway that may have a causal role in treatment-resistant cancers, microarray and proteomics data were collected from available literature demonstrating association of subset of these genes named as interferon-stimulated-genes (ISG) with oncogenesis and tumor radio/chemoresistance. Association in this case refers to differential expression of interferon-stimulated genes in tumors versus normal tissues or in chemoresistant and/or radioresistant cell lines versus sensitive cell lines, or induction of interferon-stimulated genes by chemotherapy and radiotherapy To elucidate the downstream interferon-stimulated genes that contributes to a more aggressive and therapy-resistant (ionizing radiation and chemotherapy) phenotype, the Interferome and GEO databases (see, respectively, Pitroda S P, Khodarev N N, Beckett M A, Kufe D W, Weichselbaum R R. MUC1-induced alterations in a lipid metabolic gene network predict response of human breast cancers to tamoxifen treatment. Proc Natl Acad Sci USA 2009; 106:5837-41; and Keller S M, Adak S, Wagner H, Herskovic A, Komaki R, Brooks B J, et al. A randomized trial of postoperative adjuvant therapy in patients with completely resected stage II or IIIA non-small-cell lung cancer. Eastern Cooperative Oncology Group. N Engl J Med 2000; 343:1217-22) were initially screened to identify 787 genes that were differentially expressed in chemoresistant and radioresistant tumors or responded to radio-chemotherapy. A literature review and review of the Interferome database was then used to identify interferon-stimulated genes (ISGs) that have been shown to be associated with an aggressive phenotype or resistance to therapy (ionizing radiation or chemotherapy). Eleven studies were identified (see Table No. 1) that described interferon-stimulated genes associated with resistance to DNA-damage or a poor clinical prognosis.

TABLE No. 1

Studies Describing Interferon-stimulated Genes

| Study No. | ISG Study |
|---|---|
| 1 | Sawyer TE, Bonner JA, Gould PM, Foote RL, Deschamps C, Trastek VF, et al. Effectiveness of postoperative irradiation in stage IIIA non-small cell lung cancer according to regression tree analyses of recurrence risks. Ann Thorac Surg 1997; 64: 1402-7; discussion 7-8. |
| 2 | Stephens RJ, Girling DJ, Bleehen NM, Moghissi K, Yosef HM, Machin D. The role of post-operative radiotherapy in non-small-cell lung cancer: a multicentre randomised trial in patients with pathologically staged T1-2, N1-2, M0 disease. Medical Research Council Lung Cancer Working Party. British journal of cancer 1996; 74: 632-9. |
| 3 | MacDermed DM, Khodarev NN, Pitroda SP, Edwards DC, Pelizzari CA, Huang L, et al. MUC1-associated proliferation signature predicts outcomes in lung adenocarcinoma patients. BMC Med Genomics 2010; 3: 16. |
| 4 | Khodarev NN, Pitroda SP, Beckett MA, MacDermed DM, Huang L, Kufe DW, et al. MUC1-induced transcriptional programs associated with tumorigenesis predict outcome in breast and lung cancer. Cancer Res 2009; 69: 2833-7. |
| 5 | Khodarev NN, Minn AJ, Efimova EV, Darga TE, Labay E, Beckett M, et al. Signal transducer and activator of transcription 1 regulates both cytotoxic and prosurvival functions in tumor cells. Cancer Res 2007; 67: 9214-20. |
| 6 | Khodarev NN, Roach P, Pitroda SP, Golden DW, Bhayani M, Shao MY, et al. STAT1 pathway mediates amplification of metastatic potential and resistance to therapy. PLoS One 2009; 4: e5821. |
| 7 | Pardanani A, Vannucchi AM, Passamonti F, Cervantes F, Barbui T, Tefferi A. JAK inhibitor therapy for myelofibrosis: critical assessment of value and limitations. Leukemia; 25: 218-25. |

TABLE No. 1-continued

Studies Describing Interferon-stimulated Genes

| Study No. | ISG Study |
|---|---|
| 8 | Wernig G, Kharas MG, Okabe R, Moore SA, Leeman DS, Cullen DE, et al. Efficacy of TG101348, a selective JAK2 inhibitor, in treatment of a murine model of JAK2V617F-induced polycythemia vera. Cancer Cell 2008; 13: 311-20. |
| 9 | Fridman JS, Scherle PA, Collins R, Burn TC, Li Y, Li J, et al. Selective inhibition of JAK1 and JAK2 is efficacious in rodent models of arthritis: preclinical characterization of INCB028050. J Immunol; 184: 5298-307. |
| 10 | Garber K. Pfizer's JAK inhibitor sails through phase 3 in rheumatoid arthritis. Nat Biotechnol 2011 29: 467-8. |
| 11 | Sun Y, Moretti L, Giacalone NJ, Schleicher S, Speirs CK, Carbone DP, et al. Inhibition of JAK2 signaling by TG101209 enhances radiotherapy in lung cancer models. J Thorac Oncol 2011 6: 699-706. |

In addition, two published papers (Hsu H S, Lin J H, Hsu T W, Su K, Wang C W, Yang K Y, et al. Mesenchymal stem cells enhance lung cancer initiation through activation of IL-6/JAK2/STAT3 pathway. Lung cancer (Amsterdam, Netherlands) 2012; 75:167-77; Zhao M, Gao F H, Wang J Y, Liu F, Yuan H H, Zhang W Y, et al. JAK2/STAT3 signaling pathway activation mediates tumor angiogenesis by upregulation of VEGF and bFGF in non-small-cell lung cancer. Lung cancer (Amsterdam, Netherlands) 2011; 73:366-74) and unpublished data from our laboratory were used to identify candidate downstream interferon-stimulated genes. Genes were included in the final screening set if they were identified in the IRDS or if they were reported in greater than or equal to two other studies. In total, 89 candidate interferon-stimulated genes were identified as shown below in Table No. 2.

TABLE No. 2

Candidate Interferon-stimulated Genes

| Gene Symbol | Entrez Gene Name | Entrez Gene ID for Human |
|---|---|---|
| ABCC3 | ATP-binding cassette, sub-family C (CFTR/MRP), member 3 | 8714 |
| B2M | beta-2-microglobulin | 567 |
| BST2 | bone marrow stromal cell antigen 2 | 684 |
| CCL2 | chemokine (C-C motif) ligand 2 | 6347 |
| CCL5 | chemokine (C-C motif) ligand 5 | 6352 |
| CCNA1 | cyclin A1 | 8900 |
| CD74 | CD74 molecule, major histocompatibility complex, class II invariant chain | 972 |
| CMPK2 | cytidine monophosphate (UMP-CMP) kinase 2, mitochondrial | 129607 |
| CTSS | cathepsin S | 1520 |
| CXCL1 | chemokine (C-X-C motif) ligand 1 (melanoma growth stimulating activity, alpha) | 2919 |
| CXCL10 | chemokine (C-X-C motif) ligand 10 | 3627 |
| CXCL3 | chemokine (C-X-C motif) ligand 3 | 2921 |
| CXCL9 | chemokine (C-X-C motif) ligand 9 | 4283 |
| DAZ1 | deleted in azoospermia 1 | 1617 |
| DDX58 | DEAD (Asp-Glu-Ala-Asp) box polypeptide 58 | 23586 |
| DDX60 | DEAD (Asp-Glu-Ala-Asp) box polypeptide 60 | 55601 |
| DDX60L | DEAD (Asp-Glu-Ala-Asp) box polypeptide 60-like | 91351 |
| DHX58 | DEXH (Asp-Glu-X-His) box polypeptide 58 | 79132 |
| DTX3L | deltex 3-like (Drosophila) | 151636 |
| EIF2AK2 | eukaryotic translation initiation factor 2-alpha kinase 2 | 5610 |
| EPSTI1 | epithelial stromal interaction 1 (breast) | 94240 |
| GBP1 | guanylate binding protein 1, interferon-inducible, 67kDa | 2633 |
| GBP2 | guanylate binding protein 2, interferon-inducible | 2634 |
| HERC5 | hect domain and RLD 5 | 51191 |
| HERC6 | hect domain and RLD 6 | 55008 |
| HNMT | histamine N-methyltransferase | 3176 |
| IFI16 | interferon, gamma-inducible protein 16 | 3428 |
| IFI27 | interferon, alpha-inducible protein 27 | 3429 |
| IFI35 | interferon-induced protein 35 | 3430 |
| IFI44 | interferon-induced protein 44 | 10561 |
| IFI44L | interferon-induced protein 44-like | 10964 |
| IFI6 | interferon, alpha-inducible protein 6 | 2537 |
| IFIH1 | interferon induced with helicase C domain 1 | 64135 |
| IFIT1 | interferon-induced protein with tetratricopeptide repeats 1 | 3434 |
| IFIT2 | interferon-induced protein with tetratricopeptide repeats 2 | 3433 |
| IFIT3 | interferon-induced protein with tetratricopeptide repeats 3 | 3437 |
| IFITM1 | interferon induced transmembrane protein 1 (9-27) | 8519 |
| IFITM2 | interferon induced transmembrane protein 2 (1-8D) | 10581 |
| IFITM3 | interferon induced transmembrane protein 3 (1-8U) | 10410 |
| IGFBP3 | insulin-like growth factor binding protein 3 | 3486 |

TABLE No. 2-continued

Candidate Interferon-stimulated Genes

| Gene Symbol | Entrez Gene Name | Entrez Gene ID for Human |
|---|---|---|
| IRF1 | interferon regulatory factor 1 | 3659 |
| IRF7 | interferon regulatory factor 7 | 3665 |
| IRF9 | interferon regulatory factor 9 | 10379 |
| ISG15 | ISG15 ubiquitin-like modifier | 9636 |
| LAMP3 | lysosomal-associated membrane protein 3 | 27074 |
| LGALS3BP | lectin, galactoside-binding, soluble, 3 binding protein | 3959 |
| LTK | leukocyte receptor tyrosine kinase | 4058 |
| LY6E | lymphocyte antigen 6 complex, locus E | 4061 |
| LY96 | lymphocyte antigen 96 | 23643 |
| MARCKS | myristoylated alanine-rich protein kinase C substrate | 4082 |
| MCL1 | myeloid cell leukemia sequence 1 (BCL2-related) | 4170 |
| MGP | matrix Gla protein | 4256 |
| MX1 | myxovirus (influenza virus) resistance 1, interferon-inducible protein p78 (mouse) | 4599 |
| MX2 | myxovirus (influenza virus) resistance 2 (mouse) | 4600 |
| NLRC5 | NLR family, CARD domain containing 5 | 84166 |
| NMI | N-myc (and STAT) interactor | 9111 |
| OAS1 | 2',5'-oligoadenylate synthetase 1, 40/46 kDa | 4938 |
| OAS2 | 2'-5'-oligoadenylate synthetase 2, 69/71 kDa | 4939 |
| OAS3 | 2'-5'-oligoadenylate synthetase 3, 100 kDa | 4940 |
| OASL | 2'-5'-oligoadenylate synthetase-like | 8638 |
| PARP12 | poly (ADP-ribose) polymerase family, member 12 | 64761 |
| PLSCR1 | phospholipid scramblase 1 | 5359 |
| PRIC285 | peroxisomal proliferator-activated receptor A interacting complex 285 | 85441 |
| PSMB10 | proteasome (prosome, macropain) subunit, beta type, 10 | 5699 |
| PSMB8 | proteasome (prosome, macropain) subunit, beta type, 8 (large multifunctional peptidase 7) | 5696 |
| PSMB9 | proteasome (prosome, macropain) subunit, beta type, 9 (large multifunctional peptidase 2) | 5698 |
| RNF213 | ring finger protein 213 | 57674 |
| RSAD2 | radical S-adenosyl methionine domain containing 2 | 91543 |
| RTP4 | receptor (chemosensory) transporter protein 4 | 64108 |
| SAMD9 | sterile alpha motif domain containing 9 | 54809 |
| SAMD9L | sterile alpha motif domain containing 9-like | 219285 |
| SAMHD1 | SAM domain and HD domain 1 | 25939 |
| SP110 | SP110 nuclear body protein | 3431 |
| SRGN | serglycin | 5552 |
| STAT1 | signal transducer and activator of transcription 1, 91 kDa | 6772 |
| TAGLN | transgelin | 6876 |
| TAP1 | transporter 1, ATP-binding cassette, sub-family B (MDR/TAP) | 6890 |
| THBS1 | thrombospondin 1 | 7057 |
| TIMP3 | TIMP metallopeptidase inhibitor 3 | 7078 |
| TNFSF10 | tumor necrosis factor (ligand) superfamily, member 10 | 8743 |
| TPD52L1 | tumor protein D52-like 1 | 7164 |
| TRIM14 | tripartite motif-containing 14 | 9830 |
| TRIM21 | tripartite motif-containing 21 | 6737 |
| UBA7 | ubiquitin-like modifier activating enzyme 7 | 7318 |
| UBE2L6 | ubiquitin-conjugating enzyme E2L 6 | 9246 |
| USP18 | ubiquitin specific peptidase 18 | 11274 |
| VAMP5 | vesicle-associated membrane protein 5 (myobrevin) | 10791 |
| WARS | tryptophanyl-tRNA synthetase | 7453 |
| XAF1 | XIAP associated factor 1 | 54739 |

To screen the candidate interferon-stimulated genes, a panel of fifteen individual cancer cell lines were selected from those available in our lab, the ATCC, or affiliated laboratories (see Table No. 3, below). These cell lines were characterized for relative radioresistance using a clonogenic assay. Briefly, the cells were cultured in their appropriate media at 5% CO2 at 37° C. Optimal cell plating concentrations for a p60 dish were determined for each cell line. The majority of cell lines were plated in triplicate at concentrations of 100 cells/plate for control, 1000 cells/plate for 2 Gy, 2000 cells/plate for 5 Gy, and 3000 cells/plate for 8 Gy. Plates were irradiated 24 hours after plating with either 2, 5, or 8 Gy using a Nordion Gammacell $^{60}$Co irradiator operating at a dose rate of ~18 Gy/minute. Cells were allowed to grow for 10-21 days (depending on the cell line) until colonies were >50 cells. Plates were then fixed with formalin and stained with crystal violet. Colonies with more than 50 cells were counted. Clonogenic survival for Clonogenic data was obtained for all cell lines tested in screen.

An siRNA screen of 86 interferon stimulated genes (ISGs) was performed in a series of cancer cell lines to determine which of the candidate genes may be associated with treatment resistance in the cell lines. The final screen was conducted as follows: On day 1, Lipofectamine RNAiMAX 0.075 µL/well diluted in Opti-MEM (Life Technologies) was added using a Tecan Freedom EVO 200 robotic liquid handling station to previously prepared 384-well microplates (Corning/3712) containing immobilized pooled siRNAs (Dharmacon siGENOME) plated in triplicate for each target gene. Cells were then added using a Thermo Electron MultiDrop Combi dispenser at 500 cells/well in 50 µL of RPMI 1640 media supplemented with 10% FCS. The final siRNA concentration in each well was 50 nM. Plates were be incubated overnight at 37° C., and on day 2 were treated with ionizing radiation at a dose of either 3Gy or left untreated. Plates were incubated at 37° C. and then assayed for viability on days 3 and 4 using the highly sensitive luciferase-based CellTiterGlo assay (Promega, Madison, Wis.). Luminescent reagent was added using a Thermo Electron MultiDrop Combi, and luminescent measurements was taken 90 minutes later using Molecular Devices Analyst GT.

Cell lines tested were screened under two conditions: (A) no treatment (basal); and (B) treatment by ionizing radiation (3 Gy). A total of fifteen (15) cell lines available from the American Type Culture Collection (ATCC), representing 7 cancer types, were screened (see Table No. 3 below). Experimental endpoint was loss of cell viability as assessed by CelTiterGlo® assay (Promega, Madison, Wis.) following manufacturer's recommendations. A heat map of the screen is shown in FIG. 1.

TABLE No. 3

Cell lines.

| Cell Line | Primary Tumor |
|---|---|
| A549 | Lung |
| NCI-H226 | Lung |
| D54 | Glioblastoma multiforme |
| T98G | Glioblastoma multiforme |
| U251 | Glioblastoma multiforme |
| DU-145 | Prostate |
| CWRR1 | Prostate |
| CW22Rv1 | Prostate |
| MCF7 | Breast |
| MCF-10A | Breast |
| WiDR | Colon |
| HCT116 | Colon |
| SCC-61 | Head & Neck |
| Nu61 | Head & Neck |
| T24 | Bladder |

Interferon-stimulated genes, for which suppression led to the maximal loss of viability in the maximal amount of cell lines, were selected for further validation with individual siRNA (deconvolution).

Figure 8A:
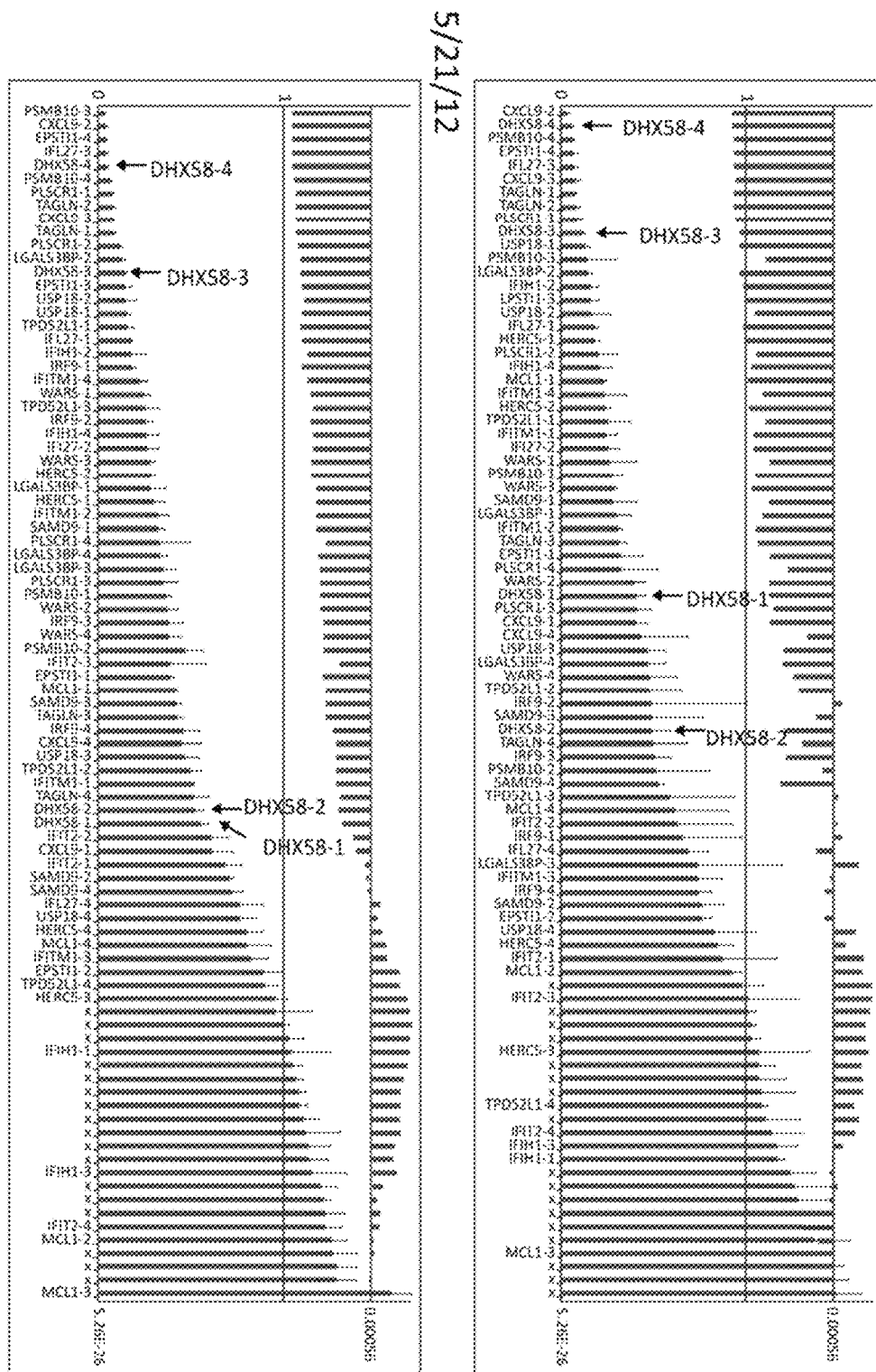
FIG. 8A shows the cell line MCF10A plated at optimal cell concentrations and reverse transfected on Day 0, incubated at 37° C. in 5% CO2 and then viability assayed at 96 hours post-transfection (no post-ionizing radiation)
Figure 8B:
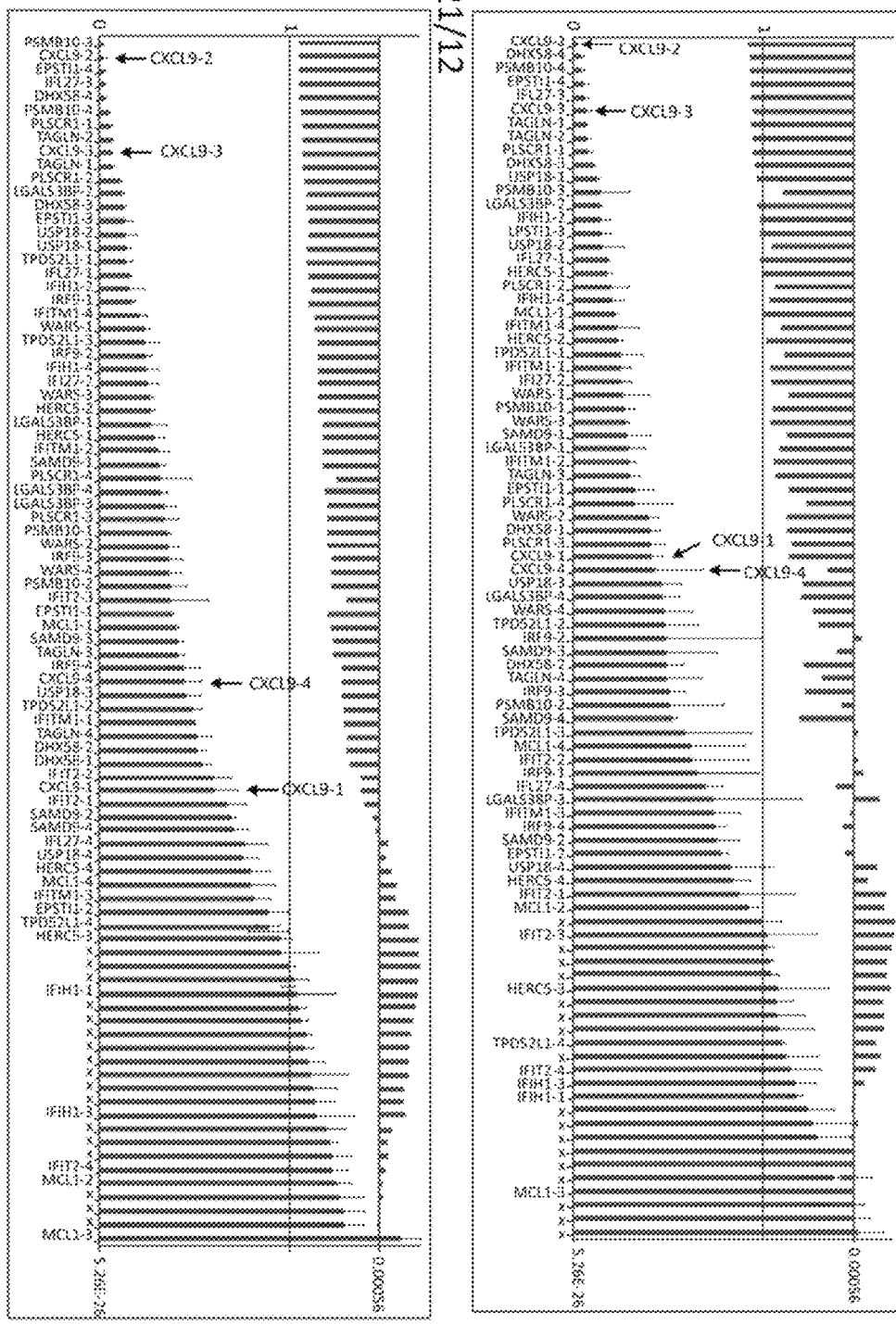
FIG. 8B shows the cell line MCF10A plated at optimal cell concentrations and reverse transfected on Day 0, incubated at 37° C. in 5% CO2, irradiated with 3 Gy at 48 hours, and then viability assayed at 96 hours post-transfection (48 hours post-ionizing radiation)
Figure 9:
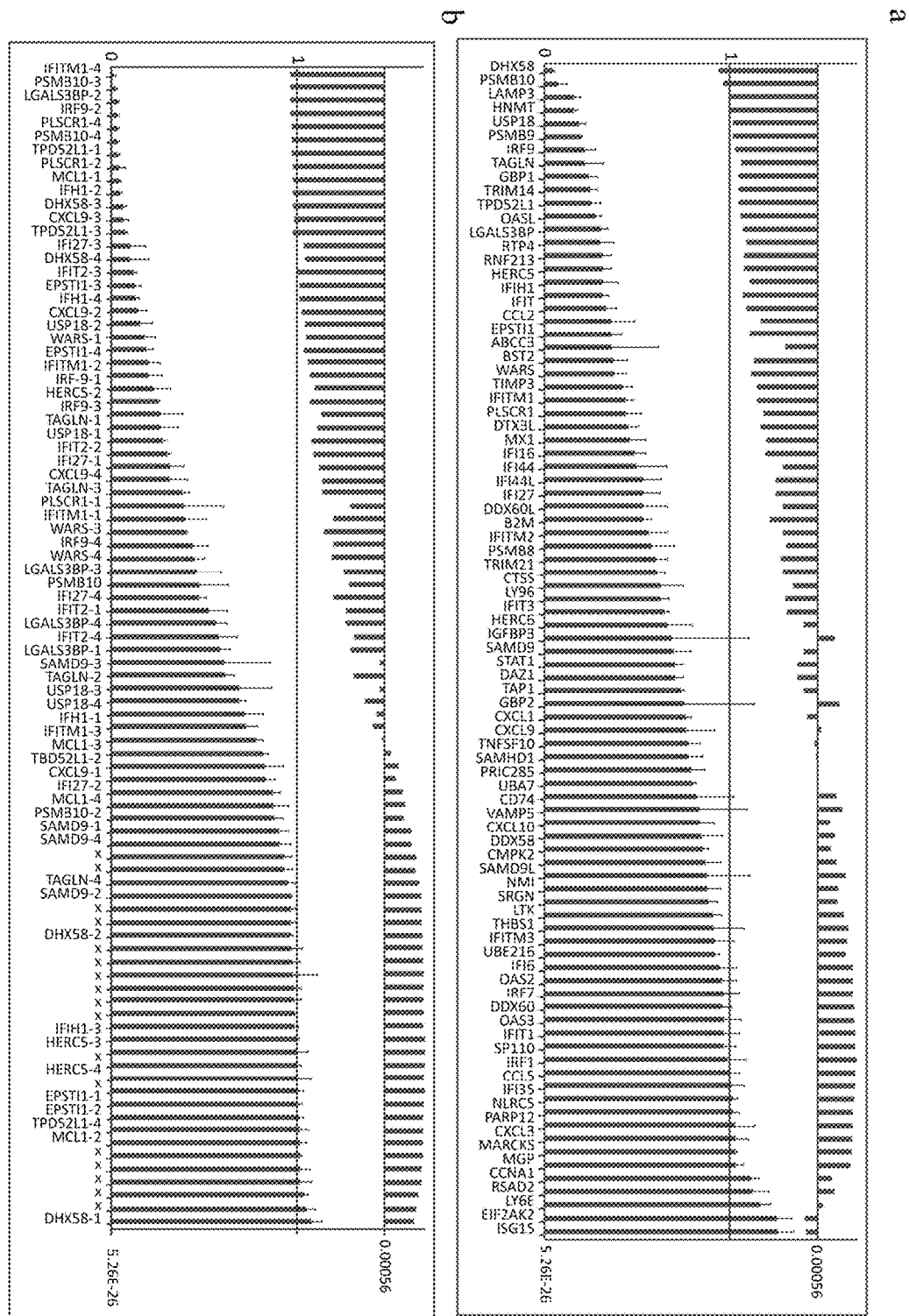
FIG. 9 shows the comparison of (a) pooled versus (b) deconvoluted siRNA suppression of viability for HCT116 treated with 3 Gy IR.

The HCT116 and MCF10A cell lines were selected for the confirmation experiment as they consistently had the highest level of viability suppression for the candidate genes. The siRNA's were deconvoluted (4 individual siRNA's per gene) and plated in triplicate. The transfection conditions used were the same as the primary screen for each cell line. The cell lines were plated at optimal cell concentrations and reverse transfected on Day 0, incubated at 37° C. in 5% CO2, irradiated with 3 Gy at 48 hours, and then viability was assayed at 120 hours post-transfection (72 hours post-ionizing radiation) using the CellTiter-Glo® Luminescent Cell Viability Assay (Promega, Madison, Wis.). This experiment was repeated to confirm reproducibility of the data (FIGS. 8A and 8B). Comparison of the pooled to the deconvoluted siRNA's demonstrates improved suppression of viability (FIG. 9). The top two siRNA's for each gene were selected for subsequent qRT-PCR confirmation experiments to exclude off-target effects. All selected candidate genes were confirmed with individual siRNAs phenotipically and by the ability to suppress gene-specific mRNA.

Based on these data, new targets were identified for the suppression of tumor growth and radiosensitization that may serve as companion targets for improved tumor response to the Jak1/Jak2-based therapy, see Table Nos. 4a and 4b.

TABLE No. 4a

Interferon-Stimulated Gene Targets for Suppression of Tumor Growth and Radiosensitization in Order of Ranking.

| List of Genes in Order of Their Ranking) | Function |
|---|---|
| DHX58 | Cytoplasmic DNA sensors |
| PLSCR1 | Bacterial toxin defense |
| USP18 | protein modification/degradation |
| PSMB10 | protein modification/degradation |
| IFITM1 | Anti-viral defense |
| OASL | Anti-viral defense |
| EPSTL1 | Extracellular matrix protein |
| LGALS3BP | Extracellular matrix protein |
| IFIH1 | Cytoplasmic DNA sensors |
| ABCC3 | Drug transporter |
| DTX3L | Other |
| PSMB9 | protein modification/degradation |
| IRF9 | Anti-viral defense |
| TAGLN | Other |
| IFIT2 | Anti-viral defense |
| TPD52L1 | Other |
| CXCL9 | Chemokine |
| GBP1 | Other |
| BST2 | Anti-viral defense |
| SP110 | Other |
| HERC5 | protein modification/degradation |
| CCL2 | Chemokine |
| WARS | Other |
| MCL1 | Anti-apoptotic mitochondria-related proteins |
| TRIM14 | Other |

TABLE No. 4b

Interferon-Stimulated Gene Targets for Suppression of Tumor Growth and Radiosensitization in Order of Functional Groups.

| List of Genes According to Functional Groups | Functions |
|---|---|
| DHX58 | anti-viral defense (recognition of viral RNA) |
| IFITM1 | anti-viral defense |
| OASL | anti-viral defense |
| IRF9 | anti-viral defense, transcription |
| BST2 | anti-viral defense |
| IFIT2 | anti-viral defense |
| IFIH1 | anti-viral defense (recognition of viral RNA) |
| PLSCR1 | bacterial toxin defense |
| PSMB9 | protein modification/degradation |
| PSMB10 | protein modification/degradation |
| USP18 | protein modification/degradation |
| HERC5 | protein modification/degradation |
| EPSTI1 | cell-ECM interaction/cytoskeleton |
| LGALS3BP | cell-ECM interaction/cytoskeleton |
| TAGLN | cell-ECM interaction/cytoskeleton |
| CXCL9 | chemokine |
| CCL2 | chemokine |
| ABCC3 | drug transporter |
| MCL1 | anti-apoptotic mitochondrial protein |
| DTX3L | other |
| TPD52L1 | other |
| GBP1 | other |
| SP110 | other |
| WARS | other |
| TRIM14 | other |

Genes in the Table No. 4a are distributed according to their rank of suppression, with the highest rank for DHX58 and a lowest rank for TRIM14. Genes in the Table No. 4b are distributed according to their functions, with bold font indicating genes that were validated in independent experiments using flow cytometry or clonogenics assays or/and in vivo xenograft models.

Results

Figure 2:
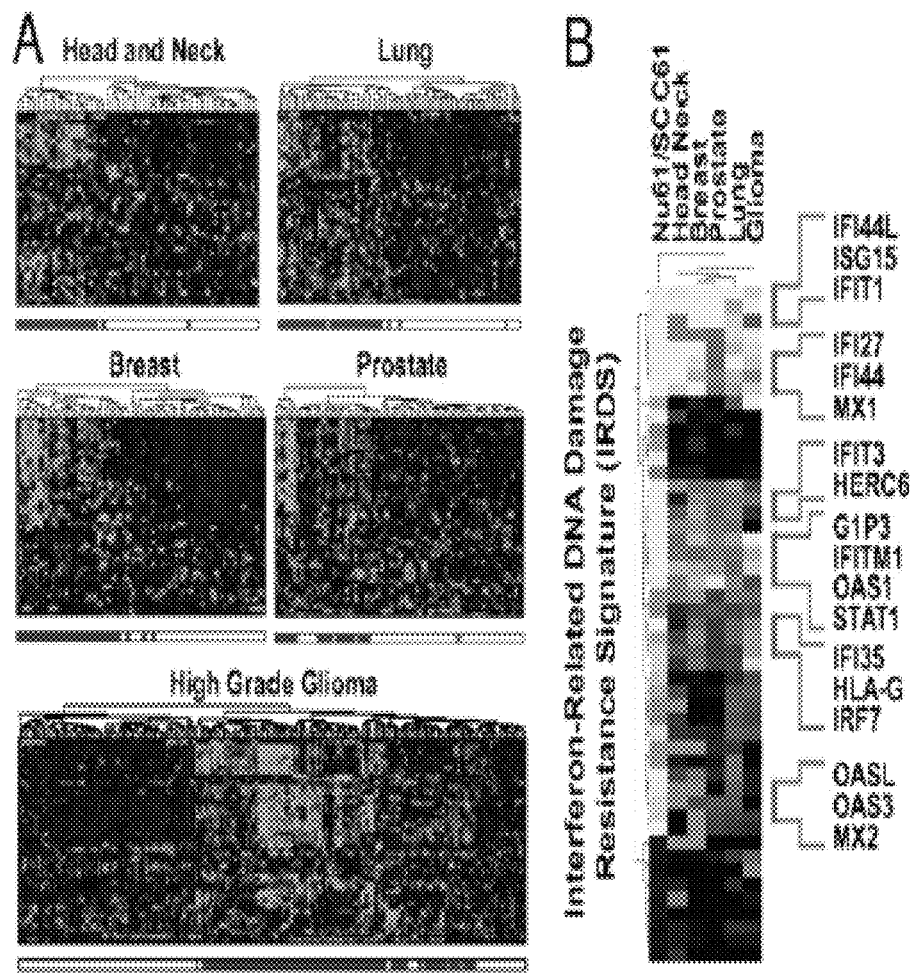
FIG. 2 shows heat maps of Interferon-Related DNA Damage Resistance Signature (IRDS)
Figure 3:
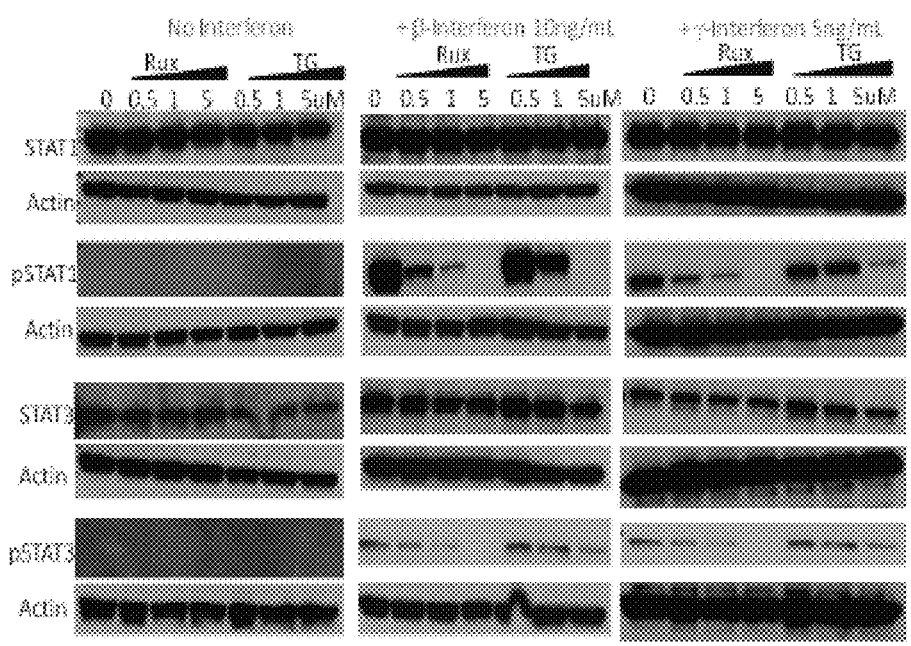
FIG. 3 shows a Western blot of SCC61 cells treated with and without the Jak2 inhibitor TG101348 (TG) and the Jak1/Jak2 inhibitor Ruxolitinib (Rux). Treatment with TG and Rux inhibited β- and γ-interferon-mediated activation of Stat1 and Stat3.

Using expressional profiling of experimental tumors in nude mice, analysis of published databases and bioinformatics approaches, constitutive expression of genes activated by Jak/Sat signaling was observed in various types of tumors and associated with aggressive tumor phenotype and radio/chemoresistance (FIG. 2). It was found that ionizing radiation activated the Jak/Stat axis in tumor cells (FIG. 3). This activation involved Stat1, Stat2, Stat3 and Stat6. Further, many down-stream genes activated by these transcription factors overlapped indicating that different Stat proteins can activate the same sets of genes or operate on the same promoter sequences. Indeed, the data herein show that Stat1 can bind to the GAS sequence in the promoter region of the Muc1 gene and activate its transcription after IFNγ stimulation (Khodarev N, Ahmad R, Rajabi H, Pitroda S, Kufe T, McClary C, et al. Cooperativity of the MUC1 oncoprotein and STAT1 pathway in poor prognosis human breast cancer. Oncogene 2010; 29:920-9). The same GAS sequence in the promoter region of Muc1 can also be occupied by Stat3 after IL6 stimulation and lead to the activation of the same oncogene (Ahmad R, Rajabi H, Kosugi M, Joshi M D, Alam M, Vasir B, et al. MUC1-C oncoprotein promotes STAT3 activation in an autoinductive regulatory loop. Science signaling 2011; 4:ra9). Therefore, Stat1 and Stat3 can operate on the same promoters thereby activating the same oncogenes, although they are triggered to respond by different signaling systems.

Figure 4:
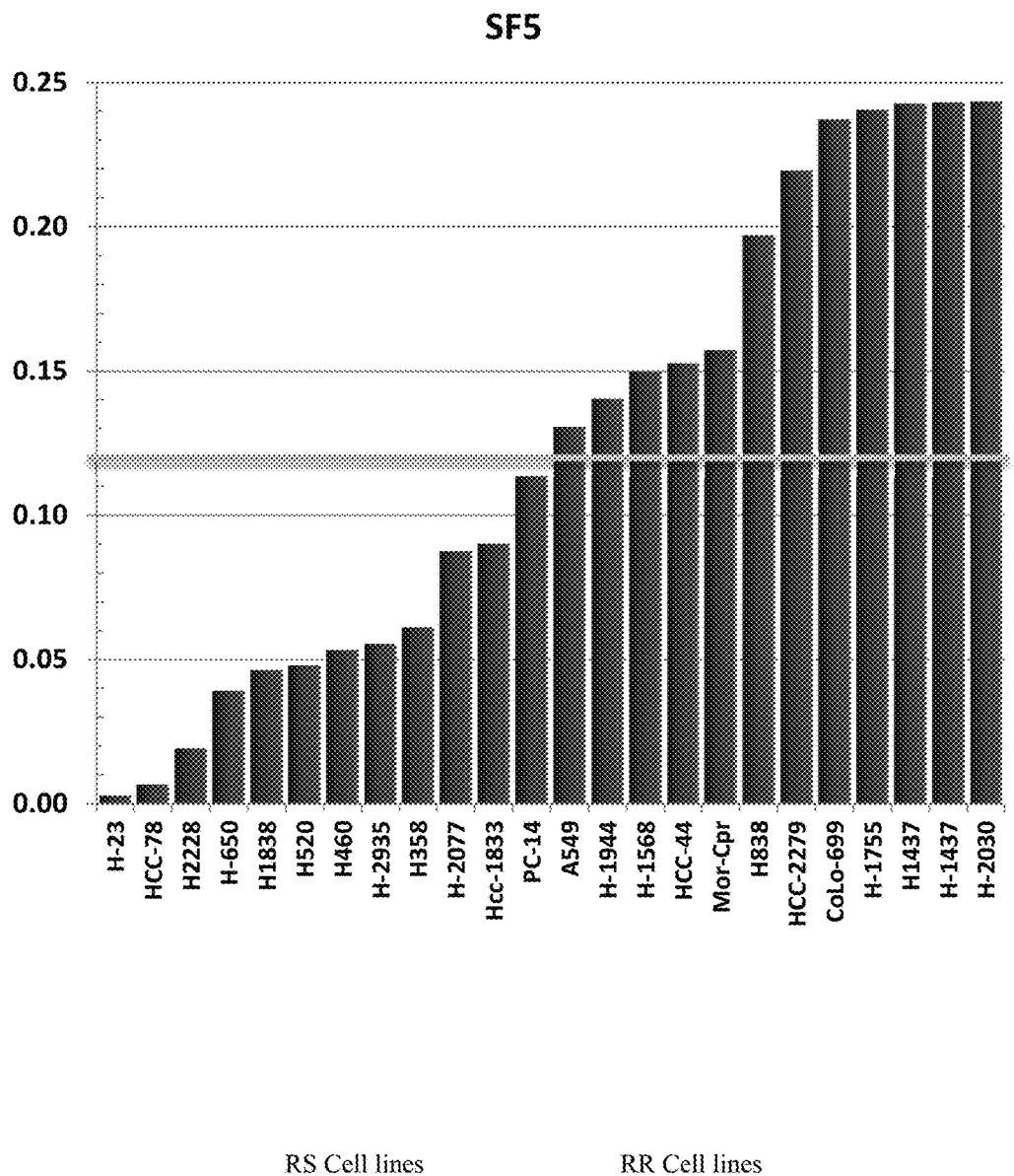
FIG. 4 illustrates the relative radioresistance of lung cancer cell lines (y-axis). Cells lines were plated and irradiated with 5 Gy. Two weeks post-irradiation, colonies were stained and counted. Data are normalized to non-irradiated samples.

The effects of Jak1/2 and Jak2 inhibitors were investigated on the activation of Stat1 and Stat3 in the context of Type I and Type II IFN signaling. FIG. 4 shows that the Jak2 inhibitor TG (SAR302503) and Jak1/Jak2 inhibitor Ruxolitinib (Rux) (Incyte Pharmaceuticals and Novarts) (CAS 941678-49-5) suppressed phosphorylation of both Stat1 and Stat3. TG101348 (SAR302503) (Sanofi-Aventis) (CAS 936091-26-8) was developed for the treatment of patients with myeloproliferative diseases including myelofibrosis, and acts as a competitive inhibitor of protein kinase JAK-2. Myelofibrosis is a myeloid malignancy associated with anemia, splenomegaly, and constitutional symptoms. TG101348 was originally discovered by TargeGen and is now under development by Sanofi-Aventis under company code SAR302503. These data suggest that the therapeutic effects of Jak2 inhibitors are associated with the suppression of the Stat1/Stat3 signaling pathways. This observation is consistent with previous observations, shown in FIGS. 3 and 4. TG more effectively suppressed tumor growth compared to Ruxolitinib in different cell lines (data not shown) and was used in all subsequent experiments.

Figure 5:
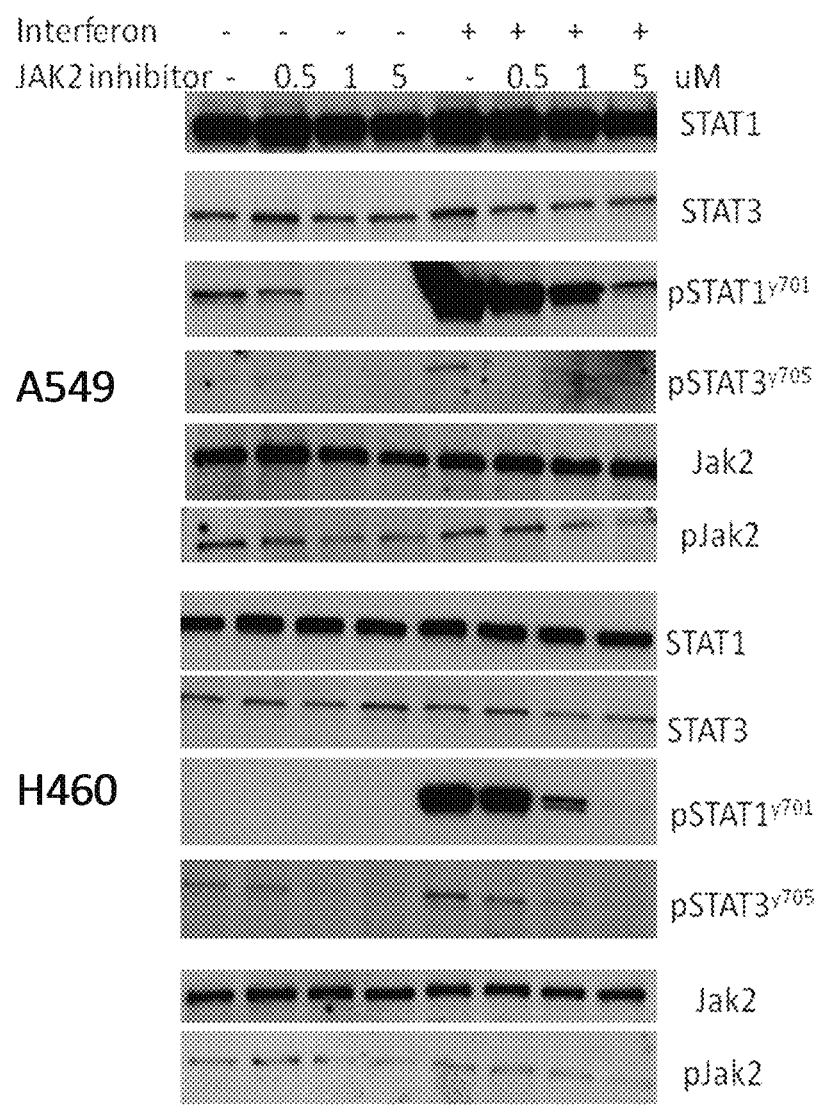
FIG. 5 shows a Western blot depicting the constitutive activation of the Jak/Stat axis in lung cancer cells and ability of Jak2 inhibitor to suppress this activation.

To further characterize the effects of Jak2 inhibition on radioresistance, the radiosensitivity of 24 lung cancer cell lines was tested using a clonogenic assay. Based on clonogenic survival at 5 Gy (SF5=surviving fraction at 5 Gy), lung cancer cell lines were arbitrarily separated into radioresistant (RR) and radiosensitive (RS) categories (FIG. 5). The relatively radioresistant (RR) cell line A549 and the relatively radiosensitive (RS) cell line H460 were further tested using Western blot analysis of the Jak/Stat pathway. Both cell lines were treated with IFNγ (10 ng/ml) and Jak2 inhibitor TG in concentrations of 0.5, 1, and 5 µM (see FIG. 5). This experiment demonstrated that both radioresistant and radiosensitive lung cancer cell lines have intact upstream Jak2 signaling leading to phosphorylation of both Stat1 and Stat3 in response to the administration of IFNγ.

Further, Stat3 was shown to respond to Type I IFN in both the radioresistant and radiosensitive cell lines. Activation of Stat3 in response to Type I IFNs is not described as the "traditional" Stat3 activating pathway and may be considered in the explanation of phenotypes associated with overexpression of the Jak/Stat axis. Moreover, these data reveal the absence of constitutively phosphorylated Stat3 in the radioresistant lung cancer cell line A549. Contrary to these observations, radioresistant A549 cells demonstrate constitutively active Stat1. However, H460, the radiosensitive lung cancer cell line, did not express pStat1 without IFN stimulation but demonstrated constitutively phosphorylated Stat3. These data suggest that in lung cancer cell lines constitutive activation of Stat1 is associated with the radioresistant phenotype, as is described elsewhere.

Figure 6:
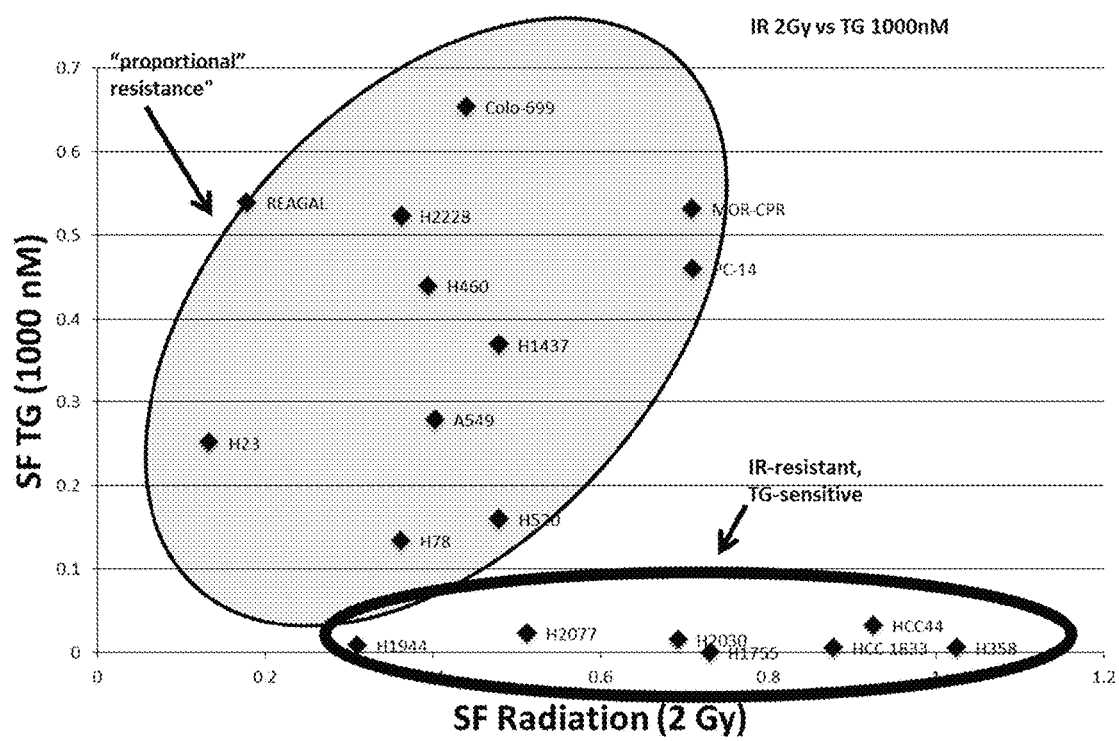
FIG. 6 shows grouping of lung cancer cell lines according to their resistance/sensitivity to SAR and ionizing radiation.
Figure 7:
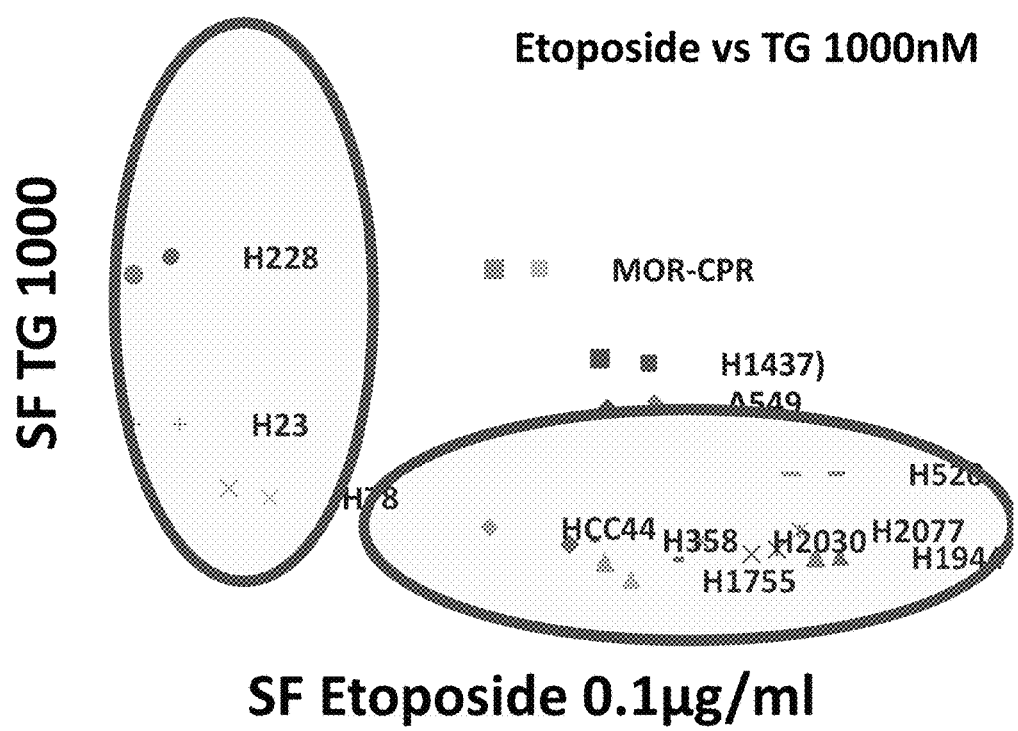
FIG. 7 shows the grouping of lung cancer cell lines according to their resistance/sensitivity to SAR and Etoposide.

It was also demonstrated that in both the A549 and H460 lung cancer cell lines, Jak2 is constitutively activated via phosphorylation (FIG. 6). These data represent important observations suggesting that Jak/Stat signaling can be activated in some lung cancer cell lines providing the rationale for further investigations using Jak2 inhibitors as a treatment modality. In subsequent experiments, 18 lung cancer cell lines were tested for sensitivity to the Jak2 inhibitor SAR302503 (TG) using a clonogenic assay. Similar to ionizing radiation resistance, it was found that lung cancer cell lines can be separated based on their relative resistance to TG (FIG. 7). Further, radioresistance was positively correlated with resistance to Jak2 suppression in 11 cell lines. However, 7 cell lines were relatively radioresistant but demonstrated high sensitivity to TG. Further, H2030 cells were the most radioresistant cells (see FIG. 5) but following treatment with 5 Gy+1 µM TG, no clonogenic colonies formed. These data suggest that some lung cancer cells with intrinsic radioresistance may be suppressed and/or radiosensitized by TG.

The relative sensitivity of lung cancer cell lines to TG and etoposide—one of the most common drugs in adjuvant chemotherapy of lung cancer was also tested. Subgroups of cell lines were found with relatively high resistance to etoposide (SF>0.5) but relatively sensitive to TG (0.1<SF<0.2; see FIG. 8). As proof of principle, two isogenic cell lines CWRR1 (pStat3-negative, without constitutive activation of Jak/Stat-signaling) and CW22Rv1 (with constitutively active Jak/Stat signaling) were established as xenografts in nude mice and treated by ionizing radiation, TG, or their combination. As is shown in FIG. 9, pStat3-negative CWRR1 was more radioresistant and was not sensitized by SAR302503. Contrary to this, pStat3-positive CW22Rv1 was successfully sensitized to ionizing radiation by TG.

Figure 10:
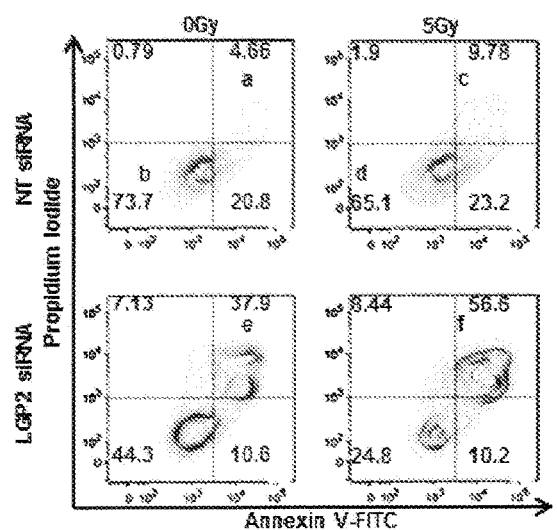
FIG. 10 shows cytometry validation of candidate target genes identified in siRNA screen. Double-positive cells, presented in the upper right quadrant of the each panel were quantified as the measure of cell death induced by siRNA suppression of the given gene without (e) or with (f) irradiation. Gene used in these experiments is DHx58 (LGP2)

Further, flow cytometry approaches may be used for independent validation of the siRNA screen (see FIG. 10). The gene used in these experiments shown in FIG. 10 was DHx58 (LGP2). Cells were transfected by individual siRNA, detected in deconvoluted screen or by non-targeting control (nt) and 24 hours post-transfection irradiated at 5Gy. Forty-eight (48) hours post-IR, cells were stained with propidium iodide (PI, vertical axis) as marker of membrane destabilization and Annexin V (horizontal axis) as marker of apoptotic cell death. Proportion of double-positive cells, presented in the upper-right quadrant of the each panel was used as a measure of cell death induced either by suppression of the targeted gene alone (e) or IR alone (c) or their combination (f).

Figure 11:
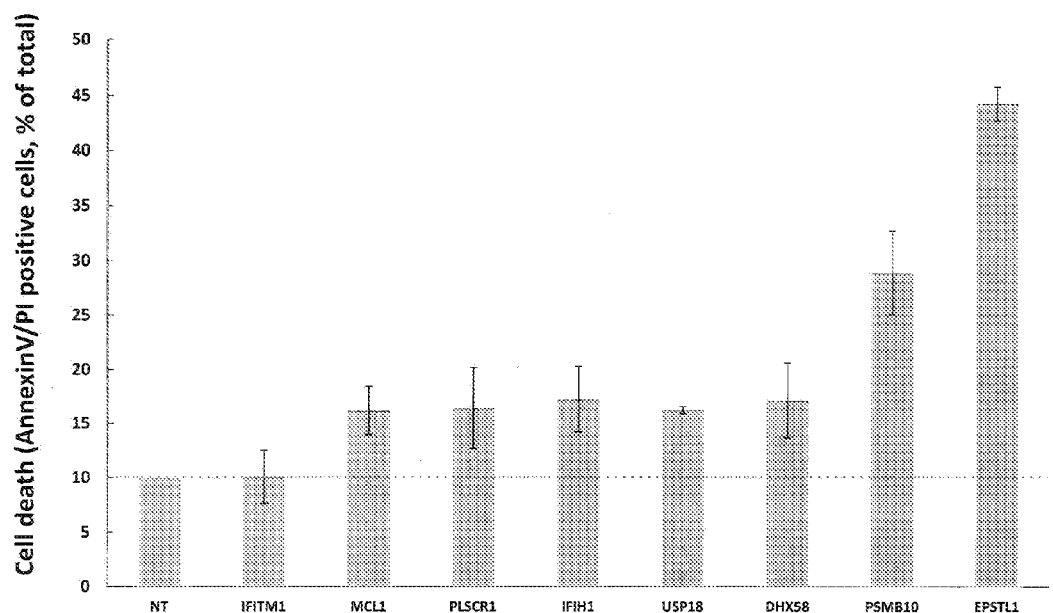
FIG. 11 shows radiosensitization of candidate genes, suppressed by individual siRNAs identified in deconvoluted screen (see FIGS. 8 and 9). Cell line HCT116 was reverse-transfected by siRNAs against indicated genes (see X-axis). 48 hours post-transfection cells were irradiated at 3Gy and 48 hours post-IR cells were stained with propidium iodide (PI) and Abs against Annexin V. Samples were analyzed on a FACSCanto flow cytometer (BD Biosciences), and data were analyzed with FlowJo software (TreeStar, Inc.). Shown are amounts of the double-positive dead cells (see FIG. 10). All experiments were done in triplicates; error bars are SDs.

We have also shown that the inhibition of identified target genes leads to significant Radiosensitization of the tumor cell line HCT116 (see FIG. 11). In this experiment the amount of cells killed by IR (5Gy) was increased in colorectal cancer cells HCT116 transfected by siRNAs against indicated genes as compared to the same cells transfected by non-targeting siRNA. Shown are double-positive cells detected as is described in FIG. 10.

Figure 12:
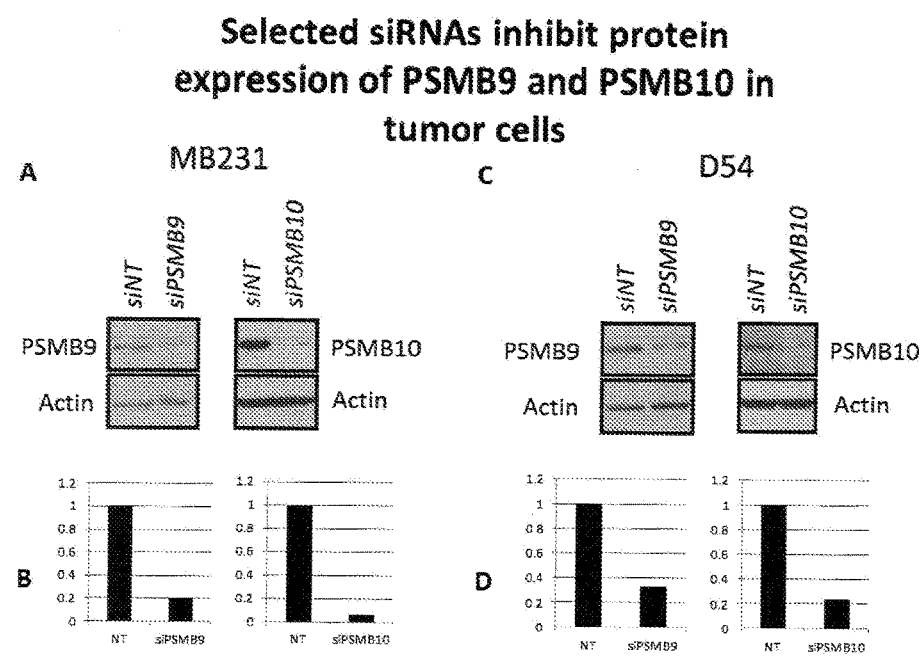
FIG. 12 shows that individual siRNA against PSMB9 and PSMB10 inhibitexpression of corresponding proteins in breast cancer tumor cell line MDA-MB-231 and glioblastoma cell line D54. Cell lines were transfected by corresponding siRNAs, lyzed 72 hours post-transfection and proteins were separated and detected by Western analysis as described in Methods. Panels A and C represent gel images and panels B and D-quantification of PSMB9 and PSMB10 protein expression (normalized to non-targeting control)
Figure 13:
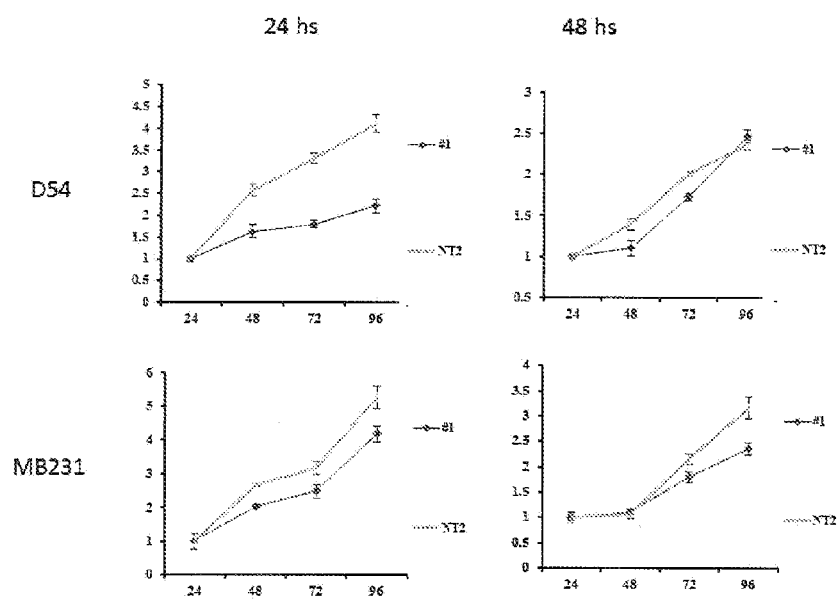
FIG. 13 shows that inhibition of PSMB9 leads to the suppression of cell growth of breast cancer cell line MDA-MB-231 and glioblastoma cell line D54; cells were transfected by siRNA against PSMB9 (#1) or non-targeting control (NT2) and 24 or 48 hours post-transfection plated in 24-well plates. Cells were counted after 24, 48, 72 and 96 hours after plating in 24 well plates. Y axis-number of cells/well, normalized to day 1; X-axis-time of cultivation, hours. Error bars are SDs between triplicated measurements.
Figure 14:
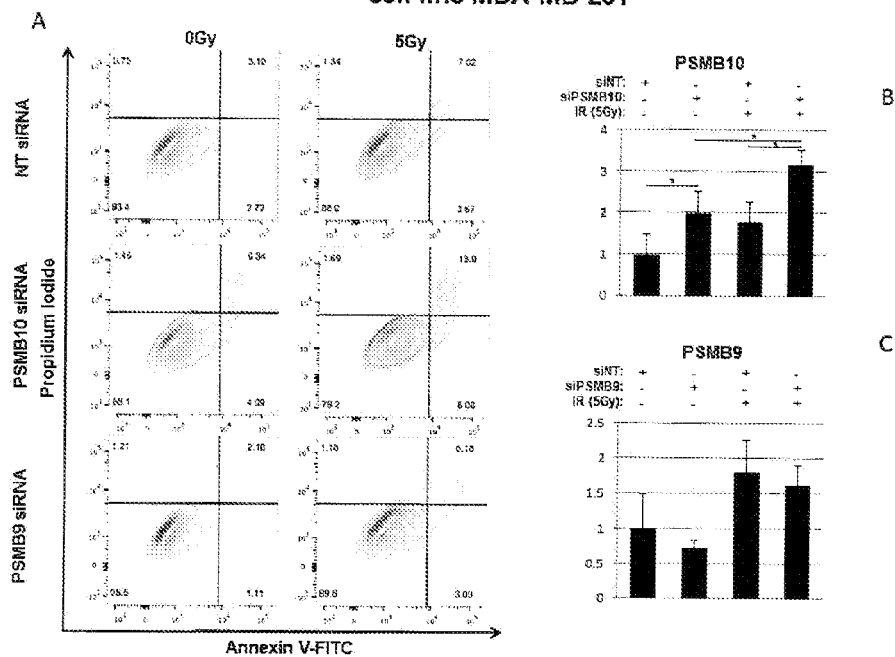
FIG. 14 shows inhibition of PSMB9 and PSMB10 that leads to the increased radiation killing of breast cancer cell line MDA-MB-231. Cells were transfected by siRNAs against PSMB9 or PSMB10, or non-targeting control; 24 hours post-transfection cells were irradiated at 5Gy and 48 hours post-IR analyzed by flow cytometry as described in FIG. 10 and FIG. 11. Panel A represents raw data and panels B and C-quantification of dead cells normalized to un-irradiated controls; Y-axis in panels B and C-fold changes related to un-irradiated cells transfected by non-targeting control). Error bars are SDs; asterisks indicate differences with p≤0.05.
Figure 15:
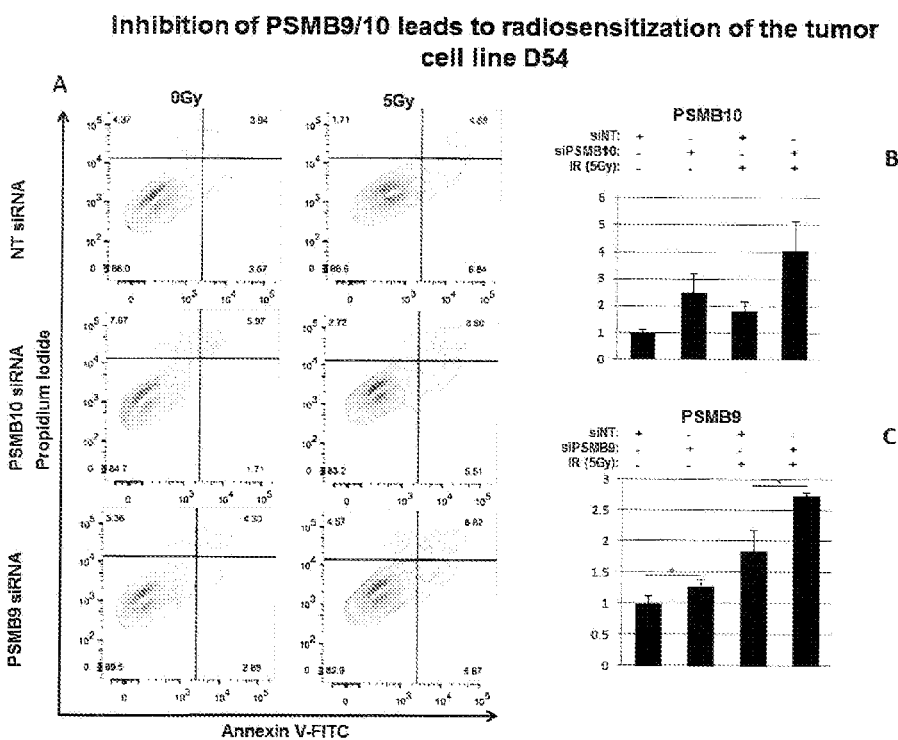
FIG. 15 shows inhibition of PSMB9 and PSMB10 that leads to the increased radiation killing of glioblastoma cell line D54; all indications are identical to FIG. 14.

Individual siRNA against PSMB9 and PSMB10 also was shown to inhibit expression of corresponding proteins in the breast cancer tumor cell line MDA-MB-231 and glioblastoma cell line D54. As seen in FIG. 12, transfection of tumor cells by individual siRNAs against PSMB9 and PSMB10 leads to the suppression of proteins encoded by these genes in breast cancer cell line MDA-MB-231 and glioblastoma cell line D54. Further, as seen in FIGS. 13-15 suppression of PSMB9 in MDA-MB-231 and D54 cell lines leads to the inhibition of their proliferation (FIG. 13); suppression of PSMB9 and PSMB10 in the breast cancer cell line MDA-MB-231 leads to the increased killing of tumor cells by IR (FIG. 14); and suppression of PSMB9 and PSMB10 in the glioblastoma cell line D54 leads to the increased killing of tumor cells by IR (FIG. 15).

Figure 16:
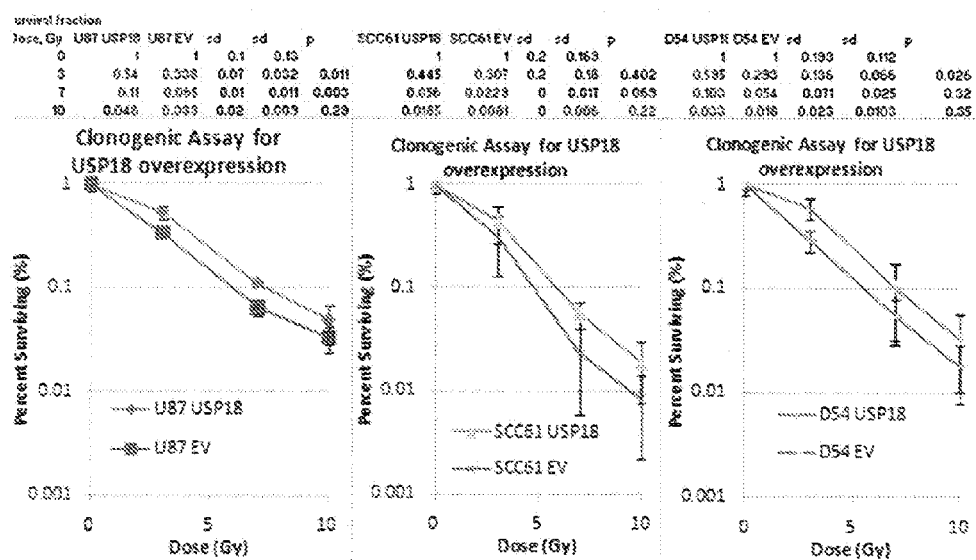
FIG. 16 shows that overexpression of USP18 leads to increased radioresistance of glioblastoma cell lines U87 and D54 and head & neck cancer cell line SCC61; differences between wild type and USP18 overexpressors were significant at 3 and 7Gy in U87; 7Gy in SCC61 and 3Gy in D54.
Figure 17:
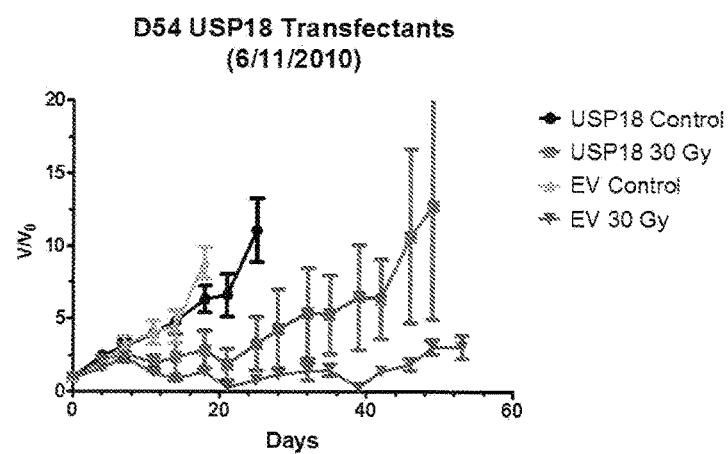
FIG. 17 shows overexpression of USP18 and increased radioresistance of xenografted D54 tumors in nude mice. Control (empty vector) and USP18-transfected cells were injected in the flanks of the nude mice; when tumors reached 200-300 mm3, they were irradiated with 6 fractions of 5Gy each (30Gy total; day 0) or left un-treated. Tumor volumes were measured once in 4 days and represented as relative tumor volume (Y-axis).

It was also demonstrated that ectopic expression of the USP18-gene, selected as a potential candidate in siRNA screen and involved in protein modifications, led to increased radioresistance of the tumor cell lines U87, D54 and SCC61 in vitro (FIG. 16). Further, it was demonstrated that D54 tumors established in nude mice and stably over-expressing USP18 were more resistant to the fractionated IR (5Gyx6 days) as compared with mock-transfected cells (FIG. 12).

It is believed that these observations provide a unique opportunity to detect the molecular properties of resistant and sensitive lung tumors to therapy with Jak2 inhibitors alone or in combination with ionizing radiation and chemotherapy. Correspondingly, these investigations may lead to the detection of biomarkers predicting individual response to Jak2/radio/chemotherapy of lung cancer.

The invention has been described in an illustrative manner and it is to be understood the terminology used is intended to be in the nature of description rather than of limitation. All patents and other references cited herein are incorporated herein by reference in their entirety. It is also understood that many modifications, equivalents, and variations of the present invention are possible in light of the above teachings. Therefore, it is to be understood that within the scope of the appended claims, the invention may be practiced other than as specifically described.

We claim:
1. A method of treating cancer in a subject by increasing the sensitivity of tumor cells of the subject to radiotherapy comprising:
    a) administering to the tumor cells a siRNA or shRNA that directly targets DHX58 mRNA in an amount that is sufficient to suppress expression of the DHX58 gene thereby increasing the sensitivity of the cells to radiotherapy; and
    b) administering to the subject a therapeutically effective amount of radiotherapy.
2. The method of claim 1 further comprising administration to the subject a therapeutically effective amount of at least one of a Jak2 or a Jak1/Jak2 inhibitor.
3. The method of claim 1 wherein DHX58 mRNA is decreased by at least 25% in tumor cells, compared to untreated cells of the same tumor.
4. The method of claim 1, wherein the radiotherapy comprises at least one of brachytherapy, external beam radiation therapy, or radiation from cesium, iridium, iodine, or cobalt.
5. The method of claim 1 further comprising administering to the tumor cells a siRNA or shRNA that directly targets mRNA of a gene selected from the group consisting of PLSCR1, USP18, PSMB10, IFITM1, OASL, EPSTL1, LGALS3BP, IFIH1, ABCC3, DTX3L, PSMB9, IRF9, TAGLN, IFIT2, TPD52L1, CXCL9, GBP1, BST2, SP110, HERC5, CCL2, WARS, MCL1, and TRIM14.

* * * * *